(12) United States Patent
Lindsay et al.

(10) Patent No.: US 12,351,855 B2
(45) Date of Patent: Jul. 8, 2025

(54) BIOELECTRONIC CIRCUITS, SYSTEMS AND METHODS FOR PREPARING AND USING THEM

(71) Applicant: ARIZONA BOARD OF REGENTS ON BEHALF OF ARIZONA STATE UNIVERSITY, Scottsdale, AZ (US)

(72) Inventors: Stuart Lindsay, Phoenix, AZ (US); Bintian Zhang, Tempe, AZ (US); Hanqing Deng, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 976 days.

(21) Appl. No.: 17/426,893

(22) PCT Filed: Jan. 30, 2020

(86) PCT No.: PCT/US2020/015931
§ 371 (c)(1),
(2) Date: Jul. 29, 2021

(87) PCT Pub. No.: WO2020/160300
PCT Pub. Date: Aug. 6, 2020

(65) Prior Publication Data
US 2022/0098635 A1    Mar. 31, 2022

Related U.S. Application Data

(60) Provisional application No. 62/799,006, filed on Jan. 30, 2019.

(51) Int. Cl.
*C12Q 1/00*    (2006.01)

(52) U.S. Cl.
CPC .................................. *C12Q 1/004* (2013.01)

(58) Field of Classification Search
CPC ........ C12Q 1/004; C12Q 1/25; C12Q 1/6825; C12Q 1/001; C12Q 1/37; C12Q 1/6869;
(Continued)

(56) References Cited

U.S. PATENT DOCUMENTS

| 5,198,543 A | 3/1993 | Blanco |
| 6,391,558 B1 | 5/2002 | Henkens et al. |

(Continued)

FOREIGN PATENT DOCUMENTS

| CN | 1325490 A | 12/2001 |
| CN | 1916630 A | 2/2007 |

(Continued)

OTHER PUBLICATIONS

A. Miodek, et al., "Streptavidin-polypyrrole Film as Platform for Biotinylated Redox Probe Immobilization for Electrochemical Immunosensor Application", Electroanalysis, 28(8): p. 1824-1832 (Year: 2016).*

(Continued)

*Primary Examiner* — J. Christopher Ball
(74) *Attorney, Agent, or Firm* — Casimir Jones, S.C.; Peter J. Schlueter

(57) ABSTRACT

A universal connection system for assembling and electrically connecting proteins to make bioelectronic detectors and logic circuits, exploiting the electronic properties of ligand-receptor interactions and the quasi metallic properties of protein interiors.

15 Claims, 21 Drawing Sheets

Specification includes a Sequence Listing.

(58) Field of Classification Search
CPC ........ C12Q 2521/101; C12Q 2521/543; C12Q 2563/116; C12Q 2563/131; C12Q 2565/607; C12Q 2521/301; C12Q 2521/513; G01N 33/5438; G01N 2333/9125; G01N 27/3272; G01N 33/6803

See application file for complete search history.

(56) References Cited

U.S. PATENT DOCUMENTS

| | | |
|---|---|---|
| 6,824,974 B2 | 11/2004 | Pisharody et al. |
| 7,632,671 B2 | 12/2009 | Tong |
| 7,785,785 B2 | 8/2010 | Pourmand et al. |
| 8,628,649 B2 | 1/2014 | Lindsay et al. |
| 8,753,893 B2 | 6/2014 | Liu et al. |
| 8,961,757 B2 | 2/2015 | Nuckolls et al. |
| 8,968,540 B2 | 3/2015 | Reinhart et al. |
| 9,140,682 B2 | 9/2015 | Lindsay et al. |
| 9,274,430 B2 | 3/2016 | Gyarfas et al. |
| 9,376,713 B2 | 6/2016 | Bashir et al. |
| 9,395,352 B2 | 7/2016 | Lindsay et al. |
| 9,593,372 B2 | 3/2017 | Lindsay et al. |
| 9,766,248 B2 | 9/2017 | Lindsay et al. |
| 9,810,681 B2 | 11/2017 | Lindsay et al. |
| 9,938,586 B2 | 4/2018 | Liang et al. |
| 10,036,064 B2 | 7/2018 | Merriman et al. |
| 10,047,392 B2 | 8/2018 | Ivankin et al. |
| 10,051,722 B2 | 12/2018 | Jin et al. |
| 10,227,694 B2 | 3/2019 | Jin et al. |
| 10,378,103 B2 | 8/2019 | Jin et al. |
| 10,379,102 B2 | 8/2019 | Lindsay et al. |
| 10,422,787 B2 | 9/2019 | Lindsay et al. |
| 10,508,296 B2 | 12/2019 | Merriman et al. |
| 10,526,696 B2 | 1/2020 | Jin et al. |
| 10,584,410 B2 | 3/2020 | Jin et al. |
| 10,597,767 B2 | 3/2020 | Merriman et al. |
| 10,648,941 B2 | 5/2020 | Merriman et al. |
| 10,712,334 B2 | 7/2020 | Choi et al. |
| 10,737,263 B2 | 8/2020 | Choi et al. |
| 10,913,966 B2 | 2/2021 | Merriman et al. |
| 11,630,098 B2 | 4/2023 | Lindsay et al. |
| 11,959,905 B2 | 4/2024 | Lindsay et al. |
| 2003/0064390 A1 | 4/2003 | Schuelein et al. |
| 2003/0098248 A1 | 5/2003 | Vogel et al. |
| 2003/0124572 A1 | 7/2003 | Umek et al. |
| 2004/0146863 A1 | 7/2004 | Pisharody et al. |
| 2004/0249124 A1 | 12/2004 | Caruso et al. |
| 2005/0074871 A1 | 4/2005 | Albert et al. |
| 2005/0266456 A1 | 12/2005 | Williams et al. |
| 2005/0285275 A1 | 12/2005 | Son et al. |
| 2006/0154489 A1 | 7/2006 | Tornow et al. |
| 2008/0218184 A1 | 9/2008 | White et al. |
| 2009/0017571 A1 | 1/2009 | Nuckolls et al. |
| 2009/0215156 A1 | 8/2009 | Chung et al. |
| 2009/0226899 A1 | 9/2009 | Chen |
| 2009/0295372 A1 | 12/2009 | Krstic et al. |
| 2010/0084276 A1 | 4/2010 | Lindsay |
| 2010/0184062 A1 | 7/2010 | Steinmuller-Nethl et al. |
| 2010/0206731 A1 | 8/2010 | Lau et al. |
| 2010/0285514 A1 | 11/2010 | Claussen et al. |
| 2011/0098218 A1 | 4/2011 | Han et al. |
| 2011/0166034 A1 | 7/2011 | Kwong et al. |
| 2011/0312529 A1 | 12/2011 | He et al. |
| 2012/0228386 A1 | 9/2012 | Wu et al. |
| 2012/0258870 A1 | 10/2012 | Schwartz et al. |
| 2012/0288948 A1 | 11/2012 | Lindsay et al. |
| 2013/0109577 A1 | 5/2013 | Korlach et al. |
| 2013/0302901 A1 | 11/2013 | Lindsay et al. |
| 2014/0141525 A1 | 5/2014 | Albert et al. |
| 2014/0231274 A1 | 8/2014 | Oki et al. |
| 2015/0010935 A1 | 1/2015 | Lindsay et al. |
| 2015/0017655 A1 | 1/2015 | Huang et al. |
| 2015/0086994 A1 | 3/2015 | Williams et al. |
| 2015/0142327 A1 | 5/2015 | Ashcroft et al. |
| 2015/0144506 A1 | 5/2015 | Lindsay et al. |
| 2015/0285818 A1 | 10/2015 | Banala et al. |
| 2015/0362459 A1 | 12/2015 | Chung et al. |
| 2016/0018384 A1 | 1/2016 | Lindsay et al. |
| 2016/0025702 A1 | 1/2016 | Lindsay et al. |
| 2016/0082739 A1 | 3/2016 | Takagiwa |
| 2016/0083789 A1 | 3/2016 | Turner et al. |
| 2016/0097759 A1 | 4/2016 | Lindsay et al. |
| 2016/0108002 A1 | 4/2016 | Zhang et al. |
| 2016/0146828 A1 | 5/2016 | Lindsay et al. |
| 2016/0177383 A1 | 6/2016 | Ashcroft et al. |
| 2016/0194698 A1 | 7/2016 | Lindsay |
| 2016/0258925 A1 | 9/2016 | Gyarfas et al. |
| 2016/0280723 A1 | 9/2016 | Zhang et al. |
| 2016/0282295 A1 | 9/2016 | Wang et al. |
| 2016/0319343 A1 | 11/2016 | Korlach et al. |
| 2017/0003245 A1 | 1/2017 | Lindsay et al. |
| 2017/0016852 A1 | 1/2017 | Lindsay et al. |
| 2017/0037462 A1 | 2/2017 | Turner et al. |
| 2017/0038333 A1 | 2/2017 | Turner et al. |
| 2017/0038369 A1 | 2/2017 | Lindsay et al. |
| 2017/0044605 A1 | 2/2017 | Merriman et al. |
| 2017/0067902 A1 | 3/2017 | Zhang et al. |
| 2017/0121761 A1 | 5/2017 | Eichen et al. |
| 2017/0137389 A1 | 5/2017 | Zhang et al. |
| 2017/0168039 A1 | 6/2017 | Lindsay et al. |
| 2017/0204066 A1 | 7/2017 | Lindsay et al. |
| 2017/0276678 A1 | 9/2017 | Ervin |
| 2017/0343558 A1 | 11/2017 | Lindsay et al. |
| 2018/0031549 A1 | 2/2018 | Chen et al. |
| 2018/0051332 A9 | 2/2018 | Esfandyarpour et al. |
| 2018/0073071 A1 | 3/2018 | Ju et al. |
| 2018/0095081 A1 | 4/2018 | Albert et al. |
| 2018/0120286 A1 | 5/2018 | Lindsay et al. |
| 2018/0155773 A1 | 6/2018 | Gunderson et al. |
| 2018/0180567 A1 | 6/2018 | Li et al. |
| 2018/0305727 A1 | 10/2018 | Merriman et al. |
| 2018/0340220 A1 | 11/2018 | Merriman et al. |
| 2019/0004003 A1 | 1/2019 | Merriman et al. |
| 2019/0041355 A1 | 2/2019 | Merriman et al. |
| 2019/0094175 A1 | 3/2019 | Merriman et al. |
| 2019/0112643 A1 | 4/2019 | Aran et al. |
| 2019/0234902 A1 | 8/2019 | Lima, Jr. et al. |
| 2019/0317040 A1 | 9/2019 | Lindsay et al. |
| 2019/0309008 A1 | 10/2019 | Ju et al. |
| 2019/0330695 A1 | 10/2019 | Guo et al. |
| 2019/0376135 A1 | 12/2019 | Mandell et al. |
| 2020/0157595 A1 | 5/2020 | Merriman et al. |
| 2021/0114025 A1 | 4/2021 | De Freitas Dias et al. |
| 2021/0208127 A1 | 7/2021 | Lindsay et al. |
| 2021/0269869 A1 | 9/2021 | Lindsay |
| 2021/0325379 A1 | 10/2021 | Lindsay et al. |
| 2021/0372986 A1 | 12/2021 | Lindsay |
| 2022/0196646 A1 | 6/2022 | Lindsay et al. |
| 2022/0252542 A1 | 8/2022 | Merriman et al. |
| 2022/0316002 A1 | 10/2022 | Lindsay et al. |
| 2022/0389502 A1 | 12/2022 | Lindsay et al. |
| 2023/0243807 A1 | 8/2023 | Lindsay et al. |

FOREIGN PATENT DOCUMENTS

| | | |
|---|---|---|
| CN | 101365827 A | 2/2009 |
| CN | 101400800 A | 4/2009 |
| CN | 102414560 A | 4/2012 |
| CN | 104105797 A | 10/2014 |
| CN | 104359946 | 2/2015 |
| CN | 104955958 A | 9/2015 |
| CN | 105283560 A | 1/2016 |
| CN | 105378113 A | 3/2016 |
| CN | 107082792 A | 8/2017 |
| CN | 107666962 A | 2/2018 |
| CN | 107683337 A | 2/2018 |
| CN | 108018270 A | 5/2018 |
| CN | 109154024 A | 1/2019 |
| CN | 109891233 A | 6/2019 |
| EP | 3976814 A1 | 4/2022 |
| JP | H01248570 A | 10/1989 |
| JP | H0719927 B2 | 3/1995 |
| JP | 2012021972 A | 2/2012 |
| JP | 2016188794 A | 11/2016 |

(56) References Cited

FOREIGN PATENT DOCUMENTS

| | | |
|---|---|---|
| JP | 2018500905 A | 1/2018 |
| TW | 201409690 A | 3/2014 |
| WO | WO-9931503 A1 | 6/1999 |
| WO | WO-2012050533 A1 | 4/2012 |
| WO | WO 2013/038272 | 3/2013 |
| WO | WO 2013/154999 | 10/2013 |
| WO | WO 2014/074727 | 5/2014 |
| WO | WO 2015/130781 | 9/2015 |
| WO | WO 2015/131073 | 9/2015 |
| WO | WO 2015/161119 | 10/2015 |
| WO | WO 2015/170784 | 11/2015 |
| WO | WO 2016/100635 A1 | 6/2016 |
| WO | WO 2016/161402 | 10/2016 |
| WO | WO 2016/210386 | 12/2016 |
| WO | WO 2017/084998 | 5/2017 |
| WO | WO 2017/123416 | 7/2017 |
| WO | WO 2017/189930 | 11/2017 |
| WO | WO 2018/026855 | 2/2018 |
| WO | WO-2018098286 A1 | 5/2018 |
| WO | WO 2018/132457 | 7/2018 |
| WO | WO 2018/200687 | 11/2018 |
| WO | WO 2018/208505 | 11/2018 |
| WO | WO 2019/046589 | 3/2019 |
| WO | WO 2019/086305 | 5/2019 |
| WO | WO 2018/217600 A1 | 11/2019 |
| WO | WO 2019/211622 | 11/2019 |
| WO | WO 2019/222527 | 11/2019 |
| WO | WO 2020/160300 | 8/2020 |
| WO | WO-2020160300 A9 | 10/2020 |
| WO | WO 2020/243207 | 12/2020 |
| WO | WO 2020/257654 | 12/2020 |
| WO | WO 2021/163275 | 8/2021 |
| WO | WO 2021/173681 | 9/2021 |
| WO | WO 2021/222791 | 11/2021 |

OTHER PUBLICATIONS

Anzai et al., "Avidin-biotin complexation for enzyme sensor applications" Trends in Analytical Chemistry, 1994, 13(5): 131-133.
Barhoumi et al: "Urease immobilization on biotinylated polypyrrole coated ChemFEC devices for urea biosensor development" IRBM, Apr. 1, 2008, 29(2-3): 192-201.
Cui et al: "Layer-by-layer 1 assembly of multilayer filme composed of avidin and biotin-labeled antibody for immunosensing", Biosensors And Bioelectronics, Jan. 1, 2003, 18(1): 59-67.
Ouerghi et al., "Impedimetric immunosensor using avidin-biotin for antibody immobilization" Bioelectrochemistry, May 15, 2002, 56(1-2): 131-133.
Prodromids et al., "Impedimetric immunosensors—A review" Electrochimica Acta, May 30, 2010, 55(14): 4227-4233.
International Search Report and Written Opinion for PCT/US20/15931. Mailed Jul. 27, 2020. 17 pages.
Adhikari et al., Conductivity of individual Geobacter pili. RSC Advances, 2016. 6: p. 8354-8357.
Alloway et al., Interface Dipoles Arising from Self-Assembled Monolayers on Gold: UV-Photoemission Studies of Alkanethiols and Partially Fluorinated Alkanethiols. J. Phys. Chem. B 2003, 107:11690-11699.
Amdursky et al., Electronic transport via proteins. Adv Mater. Nov. 12, 2014;26(42):7142-61.
Aubert et al., Intraprotein radical transfer during photoactivation of DNA photolyase. Nature. Jun. 1, 2000;405(6786):586-90.
Bostick et al., Protein bioelectronics: a review of what we do and do not know. Rep Prog Phys. Feb. 2018;81(2):026601.
Chang et al., Chemical recognition and binding kinetics in a functionalized tunnel junction. Nanotechnology. Jun. 15, 2012;23(23):235101.
Chichil et al., Linkers in the structural biology of protein-protein interactions. Protein Sci. Feb. 2013;22(2):153-67.
Cui et al., Reproducible measurement of single-molecule conductivity. Science. Oct. 19, 2001;294(5542):571-4.

Fulton et al., Purification of monoclonal antibody against Ebola GP1 protein expressed in Nicotiana benthamiana. J Chromatogr A. Apr. 10, 2015;1389:128-32.
Garg et al., Interface Electrostatics Dictates the Electron Transport via Bioelectronic Junctions. ACS Appl Mater Interfaces. Dec. 5, 2018;10(48):41599-41607.

Giese et al., Direct observation of hole transfer through DNA by hopping between adenine bases and by tunnelling. Nature. Jul. 19, 2001;412(6844):318-20.

Giese et al., Long distance charge transport through DNA: quantification and extension of the hopping model. Chemphyschem. Dec. 15, 2000;1(4):195-8.

Guo et al., Tuning electronic transport via hepta-alanine peptides junction by tryptophan doping. Proc Natl Acad Sci U S A. Sep. 27, 2016;113(39):10785-90.

Harriman. Further comments on the redox potentials of tryptophan and tyrosine. Journal of Physical Chemistry 1987. 91:6102-6104.

Jeffrey, An Introduction to Hydrogen Bonding. Oxford University Press New York. 1997. TOC only. 6 pages.

Kluenker et al., Monitoring Thiol-Ligand exchange on Au nanoparticle surfaces. Langmuir. Jan. 30, 2018;34(4):1700-1710.

Lagunas et al., Long distance electron transfer through the aqueous solution between redox partner proteins. Nat Commun. Dec. 4, 2018,9(1):5157.

Lai et al., Monoclonal antibody produced in plants efficiently treats West Nile virus infection in mice. Proc Natl Acad Sci U S A. Feb. 9, 2010;107(6):2419-24.

Lai et al., Robust production of virus-like particles and monoclonal antibodies with geminiviral replicon vectors in lettuce. Plant Biotechnol J. Jan. 2012;10(1):95-104.

Leary et al., Unambiguous one-molecule conductance measurements under ambient conditions. Nano Lett. Jun. 8, 2011;11(6):2236-41.

Liu et al., Vertical T cellimmunodomincance and epitope entropy determine HIV-1 escape. J Clin Invest. Jan. 2013;123(1):380-93.

Malvankar et al., Tunable metallic-like conductivity in microbial nanowire networks. Nat Nanotechnol. Aug. 7, 2011;6(9):573-9.

Nitzan. Chemical dynamics in condensed phases. Oxford University Press., Oxford. 2006. TOC only. 13 pages.

Odella et al., Controlling Proton-Coupled Electron Transfer in Bioinspired Artificial Photosynthetic Relays. J Am Chem Soc. Nov. 14, 2018;140(45):15450-15460.

Ruiz et al., Bioengineering a Single-Protein Junction. J Am Chem Soc. Nov. 1, 2017;139(43):15337-15346.

Sano et al., Cooperative biotin binding by streptavidin. Electrophoretic behavior and subunit association of streptavidin in the presence of 6 M urea. J Biol Chem. Feb. 25, 1990;265(6):3369-73.

Sequences of amino acids as found on the world wide web at bmrb.wisc.edu/referenc/choufas. 4 pages.

Smith. The hydrophilic nature of a clean gold surface. J. Colloid Interface Science 1980. 75:51-55.

Tripkovic et al., Standard hydrogen electrode and potential of zero charge in density functional calculations. Phys. Rev. B 2011. 84:115452.

Tuchband et al., Insulated gold scanning tunneling microscopy probes for recognition tunneling in an aqueous environment. Rev Sci Instrum. Jan. 2012;83(1):015102.

Vattay et al., Quantum Criticality at the Origin of Life. Journal of Physics: Conference Series 2015. 626: p. 012023. 11 pages.

Willner et al., Mediated electron transfer in glutathione reductase organized in self-assembled monolayers on Au electrodes. J. Am. Chem. Soc., 1992. 114: p. 10965-10966.

Xiao et al., Conductance titration of single-peptide molecules. J Am Chem Soc. May 5, 2004;126(17):5370-1.

Yang et al., Plant-produced Zika virus envelope protein elicits neutralizing immune responses that correlate with protective immunity against Zika virus in mice. Plant Biotechnol J. Feb. 2018;16(2):572-580.

Zhang et al., Engineering an Enzyme for Direct Electrical Monitoring of Activity. ACS Nano. Feb. 25, 2020;14(2):1360-1368.

Zhang et al., Observation of Giant Conductance Fluctuations in a Protein. Nano Futures. 2017;1(3):035002.

(56) References Cited

OTHER PUBLICATIONS

Zhang et al., Role of contacts in long-range protein conductance. Proc Natl Acad Sci U S A. Mar. 26, 2019;116(13):5886-5891.
Ackerman et al., Massively multiplexed nucleic acid detection with Cas13. Nature. Jun. 2020;582(7811):277-282.
Altschul et al., Basic local alignment search tool. J Mol Biol. Oct. 5, 1990;215(3):403-10.
Altschul et al., Gapped BLAST and PSI-BLAST: a new generation of protein database search programs. Nucleic Acids Res. Sep. 1, 1997;25(17):3389-402.
Amdursky et al., Solid-state electron transport via cytochrome c depends on electronic coupling to electrodes and across the protein. PNAS, Apr. 15, 2014, vol. 111, No. 15, pp. 5556-5561.
Artes et al., Transistor-like Behavior of Single Metalloprotein Junctions. Nano Lett.,2012, 12(6), pp. 2679-2684 (publication date (Web): Oct. 5, 2011).
Ausubel et al. Current Protocols in Molecular Biology, John Wiley & Sons, New York, 1998. 19 pages.
Bayer et al., 3-(N-Maleimido-propionyl) Biocytin: A Versatile Thiol-Specific Biotinylating Reagent, Analytical Biochemistry, 1985, 149: 529-536.
Carter et al., Functional protein materials: beyond elastomeric and structural proteins, Polym. Chem. 2019, 10:2952-2959.
Castellarnau et al., Integrated microanalytical system based on electrochemical detection and cell positioning, Materials Science and Engineering, 2006, 26: 405-410.
Chen et al., DNA sequencing using electrical conductance measurements of a DNA polymerase, Nature Nanotechnology, May 5, 2013, pp. 1-7; https://doi.org/10.1038/nnano.2013.71. 7 pages.
Chin et al., Addition of p-Azido-I-phenylalanine to the Genetic Code of *Escherichia coli*. J. Am. Chem. Soc. 2002. 124,31, 9026-9027.
Choi et al. Site-specific inhibition of integrin alpha v beta 3-vitronectin association by a serasp-val sequence through an Arg-Gly-Asp-binding site of the integrin, Proteomics, vol. 10, Issue 1, No. Jan. 1, 2010, pp. 72-80 (First published Oct. 30, 2009).
Choi et al., Single-Molecule Lysozyme Dynamics Monitored by an Electronic Circuit, Science (2012) 335:319-324.
Dellafiore et al., Modified Nucleoside Triphosphates for In-vitro Selection Techniques. Front Chem. May 4, 2016;4:18.
Dissertation by Joshua Sadar, Top-Down and Bottom-Up Strategies to Prepare Nanogap Sensors for Controlling and Characterizing Single Biomolecules, Jul. 2019, 160 pages.
Duffy et al., Modified nucleic acids: replication, evolution, and next-generation therapeutics. BMC Biology, Sep. 2, 2020. 18:112. 14 pages.
Fairhead et al., Plug-and-play pairing via defined divalent streptavidins. J Mol Biol. Jan. 9, 2014;426(1):199-214.
Fujino et al., Chimeric RNA Oligonucleotides Incorporating Triazole-Linked Trinucleotides: Synthesis and Function as mRNA in Cell-Free Translation Reactions. J Org Chem. Oct. 7, 2016;81(19):8967-8976.
Gerrits et al., Cell-Free Synthesis of Defined Protein Conjugates by Sitedirected Cotranslational Labeling, NCBI Bookshelf. Jan. 1, 2013, Retrieved from the Internet: URL:https://ww.ncbi.nlm.nih.gov/books/NBK6497.
Gonnet et al., Exhaustive matching of the entire protein sequence database. Science. Jun. 5, 1992;256(5062):1443-5.
Hajian et al., Detection of unamplified target genes via CRISPR-Cas9 immobilized on a graphene field-effect transistor. Nat Biomed Eng. Jun. 2019;3(6):427-437.
Hays et al., Development of capacitance based immunosensors on mixed self-assembled monolayers. Sensors and Actuators B: Chemical, Apr. 26, 2006, 114(2): 1064-1070.
Hohl et al. Engineering a Polyspecific Pyrrolysyl-tRNA Synthetase by a High Throughput FACS Screen. Sci Rep. Aug. 19, 2019;9(1):11971.
Hozel et al., Trapping Single Molecules by Dielectrophoresis, Physical Review Letters, 2005, 128102-1-4.

Ihalainene et al., Application of paper-supported printed gold eletrodes for impedimetric immunosensor development, Biosensors 2013, 3:1-17.
Kotlowski, Fine discrimination of volatile compounds by graphene-immobilized odorant-binding proteins, Sensors and Actuatores B: Chemical 2018 (256): 564-72.
Krishnan et al., Long-Range Conductivity in Proteins Mediated by Aromatic Residues, ACS Phys. Chem Aug. 2023, 3:444-455.
Kyte et al., A simple method for displaying the hydropathic character of a protein. J Mol Biol. May 5, 1982;157(1):105-32.
Li et al., CRISPR-SE: a brute force search engine for CRISPR design. NAR Genom Bioinform. Feb. 23, 2021;3(1):lqab013.
Li et al., Synthesis and Photovoltaic effect on electron-withdrawing units for low band gap conjugated polymers bearing bi(thienylenevinylene) side chains. Polymers. 2019, vol. 11 iss 9 pp. 1-13.
Lindsay et al., Recognition tunneling, Nanotechnology 2010, 21:262001, 12 pp.
Lindsay. Ubiquitous Electron Transport in Non-Electron Transfer Proteins. Life (Basel). May 20, 2020;10(5):72. 13 pages.
Maalouf R. et al., Label-Free Detection of Bacteria by Electro-chemical Impedance Spectroscopy: Comparison to Surface Plasmon Resonance. Anal. Chem, May 25, 2007, vol. 79, No. 13, pp. 4879-4886.
Main et al., Design of stable alpha-helical arrays from an idealized TPR motif. Structure. May 2003;11(5):497-508.
Marakova et al., An updated evolutionary classification of CRISPR-Cas systems. Nat Rev Microbiol. Nov. 2015;13(11):722-36.
McKenzie et al., Recent progress in non-native nucleic acid modifications. Chem Soc Rev. Apr. 26, 2021;50(8):5126-5164.
Mejias et al., Controlled nanometric fibers of self-assembled designed protein scaffolds. Nanoscale. Oct. 7, 2014;6(19):10982-8.
Metsky et al., Diagnostic design with machine learning model-based optimization. bioRxiv 2020.11.28.401877: 95 pages.
Mullegama et al., Nucleic Acid Extraction from Human Biological Samples. Methods Mol Biol 2019;1897:359-383.
Olsen et al., Electronic Measurements of Single-Molecule Processing by DNA Polymerase I (Klenow Fragment), Journal of the American Chemical Society (Apr. 30, 2013); pp. 1-12; DOI: 10.1021/ja311603r.
Pang et al. Fixed-Gap Tunnel Junction for Reading DNA Nucleotides, ACS Nano, 2014, 8(12), pp. 11994-12003 (Publication Date (Web): Nov. 7, 2014).
Pearson. Using the FASTA program to search protein and DNA sequence databases. Methods Mol Biol. 1994;24:307-31.
Quast et al., Cotranslational incorporation of non-standard amino acids using cell-free protein synthesis. FEBS Lett. Jul. 8, 2015;589(15):1703-12.
Sambrook et al., Molecular Cloning: A Laboratory Manual, 3d ed., Cold Spring Harbor Press, 2001. TOC only. 23 pages.
Seifert, Characterization of Streptavidin Binding to Biotinylated, Binary Self-Assembled Thio Monolayers-Influence of Component Ratio and Solvent, Langmuir, 2010, 26(9): 6386-93.
Sek et al., Conductance of alpha-helical peptides trapped within molecular junctions. J Phys Chem B. Oct. 5, 2006;110(39):19671-7.
Sela-Culang et al., The strutural basis of antibody-antigen recognition, Frontiers in Immunology, 2013, vol. 4, 13 pages.
Shimura & Yoshida, Heterogeneous photocatalytic hydrogen production from water and biomass derivatives, Energy Environmental Science 2011, 4: 2467.
Staals et al., RNA targeting by the type III-A CRISPR-Cas Csm complex of Thermus thermophilus. Mol Cell. Nov. 20, 2014;56(4):518-30.
Uygun et al., CRISPR-dCAS9 powered impedimetric biosensor for label-free detection of circulating tumor DNAs, Analytica Chimica Acta 2020, 1121:35-41.
Vaish et al., A novel, modification-dependent ATP-binding aptamer selected from an RNA library incorporating a cationic functionality. Biochemistry. Jul. 29, 2003;42(29):8842-51.
Varga et al., Binding of a Mouse Monoclonal IgE (anti-DNP) antibody to radio-derivatized polystyrene-DNP complexes, The FASEB Journal, Federation of American Societies for Experimental Biology, Jun. 1, 1990, 4(9): 2678-2683.

(56) References Cited

OTHER PUBLICATIONS

Yoon, Hidden Markov Models and their Applications in Biological Sequence Analysis, Current Genomics, 2009, 10:402-415.
Zhang et al., Electronic Conductance Resonance in Non-Redox-Active Proteins. J Am Chem Soc. Apr. 1, 2020;142(13):6432-6438.
Zhang et al., Electronic Decay Length in a Protein Molecule. Nano Lett. Jun. 12, 2019;19(6):4017-4022.
Zhang et al., Electronic Transport in Molecular Wires of Precisely Controlled Length Built from Modular Proteins, ACS Nano 2022, 16(1):1671-1680.
Zwolak et al. Electronic Signature of DNA Nucleotides via Transverse Transport, NanoLett., 2005, 5(3), pp. 421-424 (Publication Date (Web): Feb. 12, 2005).
Arielly R., et al., "Real-Time Detection of Redox Events in Molecular Junctions," Journal of the American Chemical Society, Jan. 27, 2014, vol. 136, No. 6, pp. 2674-2680.
Artes J.M., et al., "Conductance Switching in Single Wired Redox Proteins," Small, Jul. 9, 2014, vol. 10, No. 13, pp. 2537-2541, Published Online: Mar. 13, 2014.
Beratan D.N., et al., "Charge Transfer in Dynamical Biosytems, or The Treachery of (Static) Images," Accounts of Chemical Research, Feb. 17, 2015, vol. 48, No. 2, pp. 474-481, (Published on: Oct. 13, 2014).
Bertazzon A., et al., "Scanning Tunneling Microscopy Imaging of Torpedo Acetylcholine Receptor," Proceedings of the National Academy of Sciences, USA, Oct. 15, 1992, vol. 89, No. 20, pp. 9632-9636.
Bogomolny E., et al., "Structure of Wave Functions of Pseudointegrable Billiards," Physical Review Letters, Jun. 18, 2004, vol. 92, No. 24, pp. 244102-1-1244102-4, (Published on: Jun. 16, 2004).
Bogomolny E.B., et al., "Models of Intermediate Spectral Statistics," Physical Review E, Feb. 1, 1999, vol. 59, No. 2, pp. R1315-R1318.
Chang S., et al., "Gap Distance and Interactions in a Molecular Tunnel Junction," Journal of American Chemical Society, 2011, vol. 133, No. 36, pp. 14267-14269, (Published on Aug. 12, 2011).
Chang S., et al., "Palladium Electrodes for Molecular Tunnel Junctions," Nanotechnology, Oct. 4, 2012, vol. 23, No. 42(425202), pp. 1-5, 6 Pages.
Chen X., "Palladium as electrode in DNA sequencing," Applied Physics Letters, Aug. 9, 2013, vol. 103, No. 063306, pp. 1-4 (5 Pages).
Chen Y-S., et al., "A Protein Transistor Made of an Antibody Molecule and Two Gold Nanoparticles," Nature Nanotechnology, Mar. 2012, vol. 7, pp. 197-203 (25 Pages), (Published Online on: Feb. 26, 2012).
Co-Pending U.S. Appl. No. 62/184,776, filed Jun. 25, 2015, 24 Pages.
Dong X., et al., "(Alphav)(Beta3) Integrin Crystal Structures and Their Functional Implications," Biochemistry, Oct. 29, 2012, vol. 51, No. 44, pp. 8814-8828.
Engel G.S., et al., "Evidence for Wavelike Energy Transfer Through Quantum Coherence in Photosynthetic Systems," Nature, Apr. 12, 2007, vol. 446, No. 7137, pp. 782-786.
Extended European Search Report for European Application No. 20749683.7, mailed Jan. 11, 2023, 17 Pages.
Extended European Search Report for European Application No. 23188136.8, mailed Feb. 20, 2024, 15 Pages.
Fan F-R.F., et al., "Electrochemical Detection of Single Molecules," Science, Feb. 10, 1995, vol. 267, No. 5199, pp. 871-874 (5 Pages).
Grden M., et al., "Electrochemical Behaviour of Palladium Electrode: Oxidation, Electrodissolution and Ionic Adsorption," Electrochimica Acta, Nov. 1, 2008, vol. 53, No. 26, pp. 7583-7806, 16 Pages.
Haiss W., et al., "Thermal Gating of the Single Molecule Conductance of Alkanedithiols," Faraday Discussions, 2006, vol. 131, pp. 253-264, (Published on Oct. 4, 2005).
Hoffman R., et al., "An Extended Huckel Theory I. Hydrocarbons," The Journal of Chemical Physics, Sep. 15, 1963, vol. 39, No. 6, pp. 1397-1412 (17 Pages).

Im J.O., et al., "Electronic Single-molecule Identification of Carbohydrate Isomers by Recognition Tunnelling," Nature Communications, Dec. 21, 2016, vol. 7, Article 13868, pp. 1-7.
Karachaliou C-E., et al., "IgY Technology: Methods for Developing and Evaluating Avian Immunoglobulins for the in Vitro Detection of Biomolecules," World Journal of Methodology, Sep. 20, 2021, vol. 11, No. 5, pp. 243-262 (24 Pages).
Kumar K.S., et al., "Long-range Tunneling Processes Across Ferritin-based Junctions," Advanced Materials, Mar. 2, 2016, vol. 28, No. 9, pp. 1824-1830, (Dec. 28, 2015).
Leatherbarrow R.J., et al., "Structure of Immunoglobulin G by Scanning Tunnelling Microscopy," Journal of Molecular Biology, Sep. 20, 1991, vol. 221, No. 2, pp. 361-365.
Lloyd S., "Quantum Coherence in Biological Systems," Journal of Physics: Conference Series, 2011, vol. 302, No. 012037, pp. 1-5 (6 Pages).
Lucie S., et al., "Clustering and Internalization of Integrin (Alphav)(Beta3) With a Tetrameric RGD-synthetic Peptide," Molecular Therapy, May 2009, vol. 17, No. 5, pp. 837-843, (Published Online on Mar. 3, 2009).
Luo B-H., et al., "Structural Basis of Integrin Regulation and Signaling," Annual Review of Immunology, 2007, vol. 25, pp. 619-647 (32 Pages), (Jan. 2, 2007).
Nature: "Protein Structure" Nature Education at the Scitable by Nature Education, 2014, 4 Pages, [Retrieved on Oct. 15, 2024] Retrieved from URL: https:// www.nature.com/scitable/topicpage/protein-structure-14122136/.
Non-Final Office Action for U.S. Appl. No. 15/375,901, mailed Dec. 10, 2018, 30 Pages.
Notice of Allowance for U.S. Appl. No. 15/375,901, mailed Mar. 29, 2019, 11 Pages.
O'boyle N.M., et al., "Open Babel: An Open Chemical Toolbox," Journal of Cheminformatics, Oct. 7, 2011, vol. 3, No. 33, pp. 1-14.
Onuchic J.N., et al., "Pathway Analysis of Protein Electron-Transfer Reactions," Annual Review of Biophysics and Biomolecular Structure, 1992, vol. 21, pp. 349-377 (31 Pages).
Palecek E., et al., "Electrochemistry of Nonconjugated Proteins and Glycoproteins. Toward Sensors for Biomedicine and Glycomics," Chemical Reviews, 2015, vol. 115, No. 5, pp. 2045-2108, (Published on Feb. 9, 2015).
Pang P., et al., "Fixed-gap Tunnel Junction for Reading DNA Nucleotides," ACS Nano, Nov. 7, 2014, vol. 8, No. 12, pp. 11994-12003 (20 Pages), (Including Supporting Material).
Partial European Search Report for European Application No. 23188136.8, mailed Nov. 30, 2023, 18 Pages.
Partial Supplementary European Search Report for European Application No. 20749683.7, mailed Oct. 7, 2022, 20 Pages.
Polizzi N.F., et al., "Physical Constraints on Charge Transport Through Bacterial Nanowires," Faraday Discussions, 2012, vol. 155, pp. 43-62, (Published on Oct. 17, 2011).
Roxin A., et al., "Flexible or Fixed: A Comparative Review of Linear and Cyclic Cancer-Targeting Peptides," Future Medicinal Chemistry, Aug. 2012, vol. 4, No. 12, pp. 1601-1618.
Simmons J.G., "Generalized Formula for the Electric Tunnel Effect Between Similar Electrodes Separated by a Thin Insulating Film," Journal of Applied Physics, Jun. 1963, vol. 34, No. 6, pp. 1793-1803 (12 Pages).
Stuchebrukhov A.A., "Toward AB Initio Theory of Long-Distance Electron Tunneling in Proteins: Tunneling Currents Approach," Advances in Chemical Physics, Jan. 1, 2001, vol. 118, pp. 1-44.
Thomson N.H., et al., "Molecular Images of Cereal Proteins by STM," Ultramicroscopy, Jul. 1992, vol. 42-44, (Part B), pp. 1204-1213.
Xiong J-P., et al., "Crystal Structure of the Extracellular Segment of Integrin (Alpha)v(Beta)3 in Complex With an Arg-gly-asp Ligand," Science, Apr. 5, 2002, vol. 296, No. 5565, pp. 151-155 (6 Pages), (Published Online on Mar. 7, 2002).
Zhang B., et al., "Observation of Giant Conductance Fluctuations in a Protein," Nano Futures, 2017, vol. 1, pp. 1-15.
Zhang Y., et al., "Biological Charge Transfer via Flickering Resonance," Proceedings of the National Academy of Sciences, USA,

(56) References Cited

OTHER PUBLICATIONS

Jul. 15, 2014, vol. 111, No. 28, pp. 10049-10054, (Published Online: Jun. 25, 2014).

* cited by examiner

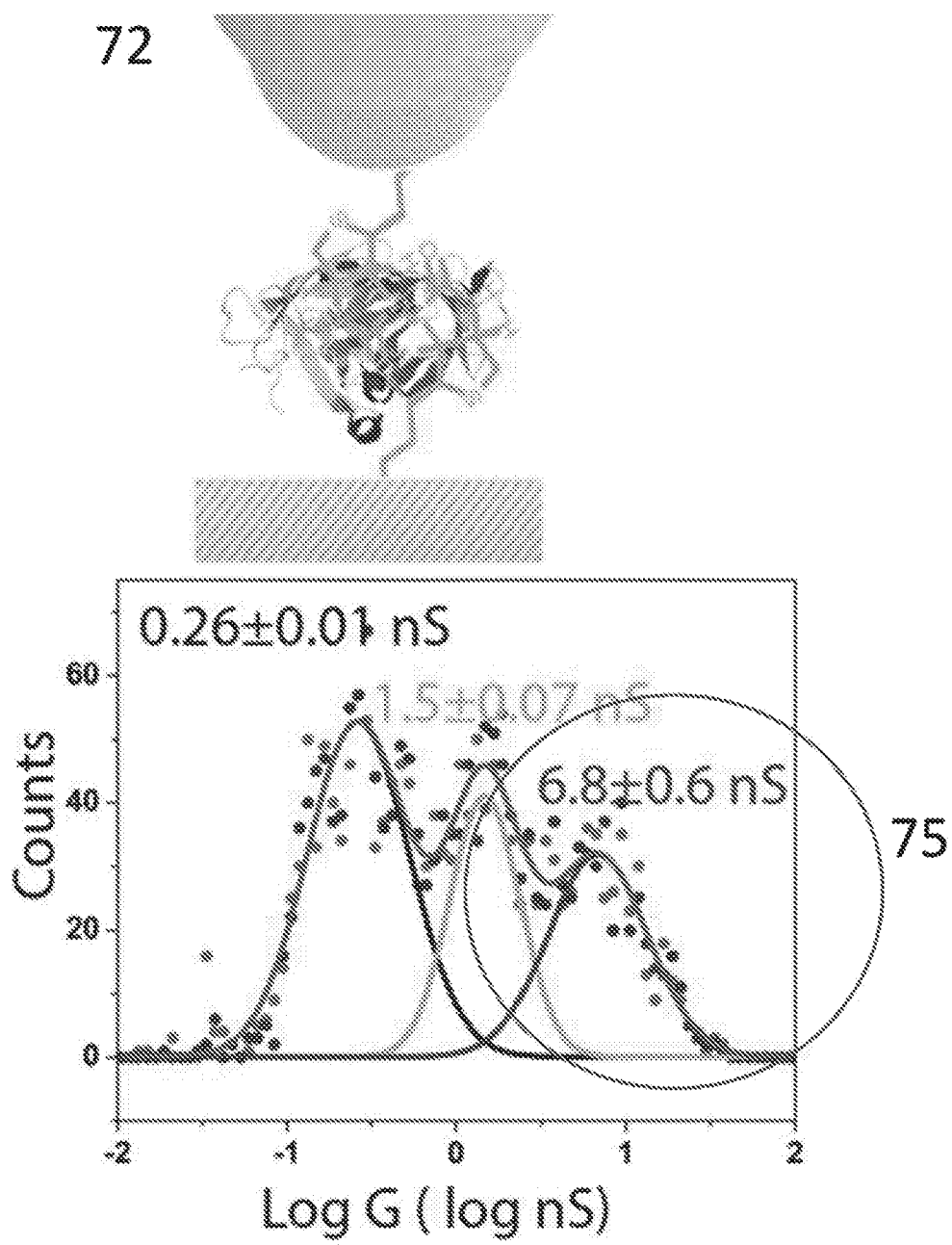

GGSGGSGGSGGS : CGTGGTAGTAGTGGTGGTAGTAGTGGTGGTAGTGGTGGTAGT
Flexible linker

Primer_F: 5'-ggcggcagcggcggcggcagcATGCCGCGTAAAATGTATAG-3'
Primer R: 5'-GTACTTCCGCGTAGTAGTcgcegtegegecegtcg-3'

Dimer formation

2avip29linker3 protein sequence (643aa, 73723.35D, pI 7.25):
MGSSHHHHHSSG▓▓▓▓▓SLNDIFEAQKIEWHE▓▓▓GDSTDGTSDGSS
MPRKMYSCAFETTTKVEDCRWAYGYMNIEDHSEYKIGNSLDEEMAWVLK
VQADLYFHNLKFAGAFIINWLERNGFKWSADGLPNTYNTIISRMGQWYMI
DICLGYKGKRKIHTVIYDSLKKLPFPVKKIAKDFKLTVLKGDIDYHKERP
VGYKITPEEYAYIKNDIQIIAEALLIQFKQGLDRMTAGSDSLKGFKDIIT
TKKFKKVFPTLSLGLDKEVRYAYRGGFTWLNDRFKEKEIGEGMVFDVNSL
YPAQMYSRLLPYGEPIVFEGKYVWDE▓▓SLNDIFEAQKIEWHE▓▓▓DYP
LHIQMIRCEFELKEGYIPTIQIKRSRFYKGNEYLKSSGGEIADLWLSNVD
LELMKEHYDLYNVEYISGLKFKATTGLFKDFIDKWTYIKTTSEGAIKQLA
KLMLNSLYGKFASNPDVTGKVPYLKENGALGFRLGEEETKDPVYTPMGVF
ITAWARYTTITAAQACYDRIIYCDTDSIHLTGTEIPDVIKDIVDPKKLGY
WAHESTFKRAKYLRQKTYIQDIYMKEVDGKLVEGSPDDYTDIKFSVKCAG
MTDKIKKEVTFENFKVGFSRKMKPKVQVPGGVVLVDDTFTIK*

106

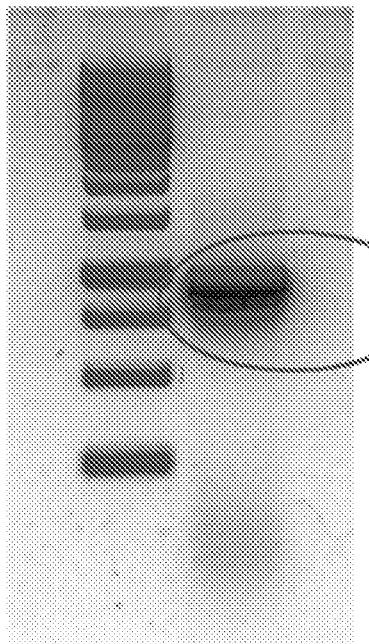

105

Fig. 10A ion under 35

SEQUENCE LISTING

```
<160> NUMBER OF SEQ ID NOS: 7

<210> SEQ ID NO 1
<211> LENGTH: 12
<212> TYPE: PRT
<213> ORGANISM: Artificial Sequence
<220> FEATURE:
<223> OTHER INFORMATION: Synthetic peptide

<400> SEQUENCE: 1

Cys Ala Leu Asp Arg Trp Glu Lys Ile Arg Leu Arg
1               5                   10

<210> SEQ ID NO 2
<211> LENGTH: 17
<212> TYPE: PRT
<213> ORGANISM: Artificial Sequence
<220> FEATURE:
```

```
<223> OTHER INFORMATION: Synthetic Peptide

<400> SEQUENCE: 2

Cys His Asn Thr Pro Val Tyr Lys Leu Asp Ile Ser Glu Ala Thr Gln
1               5                   10                  15

Val

<210> SEQ ID NO 3
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 3

Gly Asn Ser Thr Asn Gly Thr Ser Asn Gly Ser Ser
1               5                   10

<210> SEQ ID NO 4
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 4

Gly Leu Asn Asp Ile Phe Glu Ala Gln Lys Ile Glu Trp His Glu
1               5                   10                  15

<210> SEQ ID NO 5
<211> LENGTH: 38
<212> TYPE: PRT
<213> ORGANISM: Artificial Sequence
<220> FEATURE:
<223> OTHER INFORMATION: Synthetic Peptide

<400> SEQUENCE: 5

Met Gly Ser Ser His His His His His His Ser Gly Leu Val Pro
1               5                   10                  15

Arg Gly Ser Gly Leu Asn Asp Ile Phe Glu Ala Gln Lys Ile Glu Trp
                20                  25                  30

His Glu Gly Ala Ser Ser
        35

<210> SEQ ID NO 6
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 6

Gly Gly Ser Gly Gly Ser Gly Gly Ser Gly Gly Ser
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Synthetic Peptide
```

```
<400> SEQUENCE: 7

Gly Asp Ser Thr Asp Gly Thr Ser Asp Gly Ser Ser
1               5                   10
```

BIOELECTRONIC CIRCUITS, SYSTEMS AND METHODS FOR PREPARING AND USING THEM

CROSS REFERENCE TO RELATED APPLICATIONS

This application is a national phase application under 35 U.S.C. § 371 of PCT International Application No. PCT/US2020/015931, filed Jan. 30, 2020, which claims priority to and the benefit of U.S. Provisional Patent Application No. 62/799,006 filed Jan. 30, 2019, both of which are incorporated herein by reference in their entirety for all purposes.

FEDERALLY SPONSORED RESEARCH OR DEVELOPMENT

This invention was made with government support under R01 HG009180 awarded by the National Institutes of Health. The government has certain rights in the invention.

SEQUENCE LISTING

This application is being filed electronically via EFS-Web and includes an electronically submitted Sequence Listing in .txt format. The .txt file contains a sequence listing entitled "38879-252_Sequence_Listing.txt" created on Oct. 9, 2020 and is 2,160 bytes in size. The Sequence Listing contained in this .txt file is part of the specification and is hereby incorporated by reference herein in its entirety.

BACKGROUND

The use of streptavidin-biotin linkages for building molecular assemblies is well-known in the art with many reagents commercially available. It is also well-know that chemical coupling of proteins to electrodes enhances electron transfer between a metal electrode and a protein. This can take the form of a specific covalent linkage[1] or, alternately, functionalization of the electrode with a small molecule (such as an amino acid) that renders the electrode hydrophilic and thus capable of forming hydrogen bonds with a protein.[2]

While it is known that some proteins are electrically conductive over extraordinarily long distances[2-4] it has recently become clear that this conductivity is only apparent when specific chemical contacts are made between electrodes and proteins, and, in particular, connections based on the interactions of cognate ligands that interact with the hydrophobic interior of the protein that has evolved to interact with them.[5] Furthermore, this recent work showed that high electronic conductivity (nS over distances of many—2 to 20—nm) appears to be a common property of proteins, not just proteins that have evolved to carry out electron transfer functions. Such behavior is referred to herein as quasi-metallic conduction. Finally, this work also showed that the binding of a specific ligand molecule (itself bound to an electrode by a thiol linkage) to a protein, produced a better contact to the protein than direct attachment of the protein itself to the electrode via a surface thiol modification of the protein. Thus, ligands that may bind via weak and reversible bonds, but that, in doing so contact the hydrophobic interior of the protein, are better electrical connectors than strong, irreversible covalent bonds to residues on the hydrophilic exterior of the protein. The most robust recipe for making an electrical contact between a protein and an electrode, or between one protein and another, is to use the specific chemical contact that the protein has evolved to make: that is the ligand-receptor interactions. Furthermore, there are theoretical grounds[6] for believing that the interior of proteins manifests quasi metallic properties as an electronic transport material. This is consistent with Zhang et al.'s findings of conductance that is too high to measure (i.e., contact limited) in a series of proteins that are not electron transfer proteins.[5] The same properties exist in electron transfer proteins (where they might be expected on the basis of biological need). Interestingly, all the functional proteins examined have this quasi-metallic property, even though there is not, at present, known evolutionary role for it in the proteins that do not carry out electron transport functions.

SUMMARY

The present disclosure provides bioelectronic circuits, systems and methods for preparing and using them.

In one embodiment, bioelectronic circuits are provided. In one aspect of this embodiment, the bioelectronic circuit comprises (a) at least one electrode, (b) at least one ligand that is specific for a protein, wherein the ligand is modified so that it attaches to the at least one electrode, and (c) at least one protein that binds the ligand, thereby forming an electronic contact between the electrode and the protein.

In a second aspect, the bioelectronic circuit comprises (a) a first and a second electrode, (b) a first and a second ligand that are specific for a protein, wherein the ligands are modified so that the first ligand attaches to the first electrode and the second ligand attaches to the second electrode, and (c) a protein that is modified to bind the first and the second ligands, wherein the binding of the protein to the first and the second ligands forms an electronic contact between the electrode and the protein.

In a third aspect, the bioelectronic circuit comprises (a) a first and a second electrode, (b) a first ligand that is specific for a protein, wherein the first ligand is modified so that it attaches to the first electrode, (c) a protein that binds the first ligand and is modified to bind a second ligand, and (d) a second ligand that binds the protein and is modified so that it attaches to the second electrode, thereby forming an electronic contact between the first and second electrodes and the protein.

In a fourth aspect, the bioelectronic circuit comprises (a) a first and a second electrode, (b) a first protein, wherein the first protein is attached to the first electrode via biotin-streptavidin interactions, (c) a second protein, wherein the second protein is attached to the first protein via biotin-streptavidin interactions and is modified to bind a ligand, (d) a ligand that binds the second protein and is modified so that it attaches to the second electrode, thereby forming an electronic contact between the first and second electrodes and the first and second protein.

In a fifth aspect, the bioelectronic circuit comprises (a) a first and a second electrode, (b) a first and a second protein, wherein one of, or both, the first and the second proteins are attached to the first and second electrodes through biotin-streptavidin interactions, thereby forming an electronic contact between the first and the second electrodes and one of, or both, the first and the second proteins.

In a sixth aspect, the bioelectronic circuit comprises (a) a first and a second electrode, (b) a first protein, wherein the first protein is attached to the first electrode via biotin-streptavidin interactions, (c) a second protein, wherein the second protein is attached to the first protein via biotin-streptavidin interactions and is attached to the second electrode via biotin-streptavidin interactions, (d) a third protein, wherein the third protein is attached to the first and the second proteins via biotin-streptavidin interactions, thereby forming an electronic contact between the first and second electrodes and the first, second and third proteins.

In a seventh aspect, the bioelectronic circuit comprises (a) a first electrode, (b) a first protein, wherein the first protein is attached to the first electrode via biotin-streptavidin interactions, (c) a second protein, wherein the second protein is attached to the first protein via biotin-streptavidin interactions and is attached to the second electrode via biotin-streptavidin interactions, (d) a second electrode in contact with an electrolyte and connected to the first electrode, (e) a means for applying a voltage bias, (f) a means for sensing current, thereby forming an electronic contact between the first and second electrodes and the first and second proteins.

In an eighth aspect, the bioelectronic circuit is as herein described wherein the protein comprises two or more Avitag sequences placed at the surface of the protein and no more than 10 amino acid residues from tyrosines, tryptophans or histidines within the protein.

In a ninth aspect, the bioelectronic circuit comprises (a) a first and a second electrode, (b) a first and a second ligand that are specific for a protein, wherein the ligands are modified so that the first ligand attaches to the first electrode and the second ligand attaches to the second electrode, (c) a first protein and a second protein that bind the first ligand and the second ligand and (d) a third protein that is modified to bind the first and the second proteins, wherein the binding of the third protein to the first and the second proteins forms an electronic contact between the electrode and the protein.

In a tenth aspect, the bioelectronic circuit comprises (a) a first and a second electrode, (b) a first and a second ligand that are specific for a protein, wherein the ligands are modified so that the first ligand attaches to the first electrode and the second ligand attaches to the second electrode, (c) at least a first protein and a second protein that bind the first ligand and the second ligand, and may be coupled to further proteins via ligands, extending the range over which conduction is obtained.

In another embodiment, systems for electrical measurement of protein activity are provided. The system comprises (a) a bioelectronic circuit as herein described, (b) a means for applying a bias between the first and second electrode, and (c) a means for detecting the current through the bioelectronic circuit.

In another embodiment, methods of preparing bioelectronic circuits are provided. In one aspect, the method comprises (a) attaching at least one streptavidin molecule to at least one electrode, (b) introducing a biotinylated protein to the streptavidin-electrode from step (a) to form a complex comprising the at least one electrode, the at least one streptavidin molecule and the biotinylated protein.

In another embodiment, methods for detecting the activity of a polymerase, the method comprising introducing a solution of DNA template and nucleotriphosphates to any of the bioelectronic circuits as herein described, wherein polymerized product indicates that the polymerase is active.

In another embodiment, methods for detecting the activity of protein. The method comprises introducing a substrate of the protein to any of the bioelectronic circuit herein described and detecting electrical changes.

BRIEF DESCRIPTION OF THE FIGURES

FIG. 7A and FIG. 7B show a comparison of measured conductance distributions for thiolated streptavidin bound with biotin and directly coupled to electrodes with that for wild-type streptavidin bound to electrodes with the thiolated biotin shown in FIG. 2. Here, the biotin is shown exaggerated in size for clarity.

FIG. 9A and FIG. 9B show cloning constraints on the choice of protein sequence modification.

FIG. 10A and FIG. 10B shows examples of protein sequences for phi29 polymerase modified to contain two Avitag linkers showing how the incorporation of charged residues can cause misfolding.

DETAILED DESCRIPTION OF THE INVENTION

Figure 1:
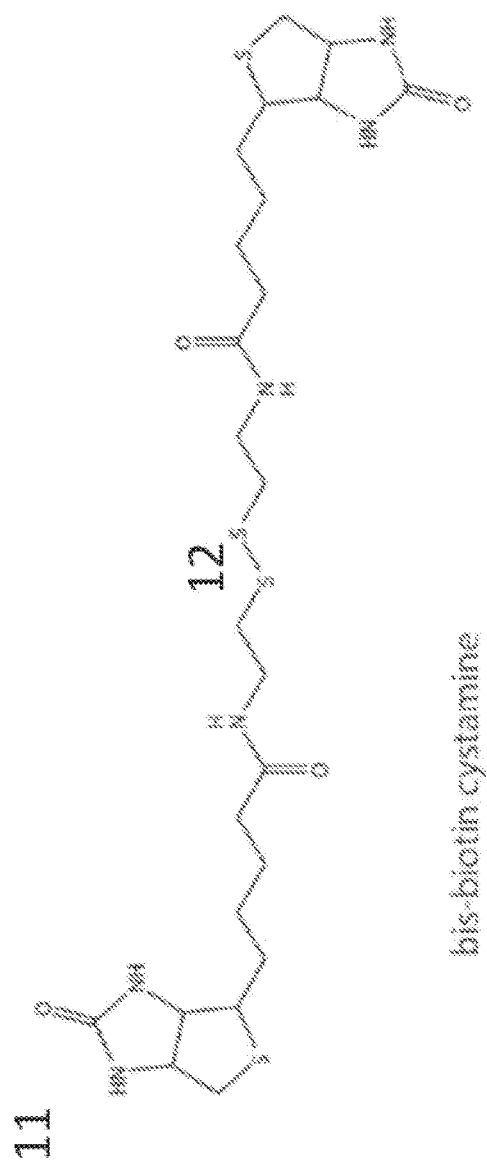
FIG. 1 shows the chemical structure of the molecule bis-biotin cystamine.

The invention includes the following:
1. A bioelectronic circuit as shown and described.
2. A system for electrical measurement of protein activity as shown and described.
3. A method for detecting the activity of a protein as shown and described.
4. A bioelectronic circuit comprising:
   (a) at least one electrode,
   (b) at least one ligand that is specific for a protein, wherein the ligand is modified so that it attaches to the at least one electrode, and
   (c) at least one protein that binds the ligand, thereby forming an electronic contact between the electrode and the protein.
5. The bioelectronic circuit according to the above 4, wherein the electrode comprises a metal selected from the group consisting of palladium, platinum or gold.

6. The bioelectronic circuit according to the above 4 or 5, wherein the ligand is selected from the group consisting of HSCH$_2$CH$_2$-dinitrophenol, CALDRWEKIRLR (SEQ ID NO: 1), CHNTPVYKLDISEATQV (SEQ ID NO: 2), cyclic RGDfC, thiolated-streptavidin, and HSCH$_2$CH$_2$-biotin.

7. The bioelectronic circuit according to any of the above 4 to 6, wherein the protein is selected from the group consisting of IgE Anti-DNP, IgG Anti-HIV, IgG Anti-Ebola, Fab Anti-Ebola, $\alpha_V\beta_3$ Integrin, and streptavidin.

8. The bioelectronic circuit according to any of the above 4 to 6, further comprising wherein the protein is a polymerase, endonuclease, helicase or a proteosome.

9. The bioelectronic circuit according to the above 4, wherein the at least one ligand is modified to comprise a thiol, amine, disulfide or cyanide moeity.

10. A bioelectronic circuit comprising:
(a) a first and a second electrode,
(b) a first and a second ligand that are specific for a protein, wherein the ligands are modified so that the first ligand attaches to the first electrode and the second ligand attaches to the second electrode, and
(c) a protein that is modified to bind the first and the second ligands, wherein the binding of the protein to the first and the second ligands forms an electronic contact between the electrode and the protein.

11. The bioelectronic circuit of the above 10, wherein the ligand is a thiolated streptavidin.

12. The bioelectronic circuit of the above 10 or 11, wherein the protein is modified to contain biotin.

13. The bioelectronic circuit of any of the above 10 to 12, wherein the protein is bis-biotinylated polymerase.

14. A bioelectronic circuit comprising:
(a) a first and a second electrode,
(b) a first ligand that is specific for a protein, wherein the first ligand is modified so that it attaches to the first electrode,
(c) a protein that binds the first ligand and is modified to bind a second ligand, and
(d) a second ligand that binds the protein and is modified so that it attaches to the second electrode, thereby forming an electronic contact between the first and second electrodes and the protein.

15. The bioelectronic circuit of the above 14, wherein the binding site on the protein to the first ligand is in proximity to a flexible linker sequence.

16. The bioelectronic circuit of the above 14, wherein the second binding site on the protein to the second ligand is in proximity to a flexible linker sequence.

17. The bioelectronic circuit of the above 15 or 16, wherein the flexible linker sequence comprises GNSTNGTSNGSS (SEQ ID NO: 3).

18. A bioelectronic circuit comprising:
(a) a first and a second electrode,
(b) a first protein, wherein the first protein is attached to the first electrode via biotin-streptavidin interactions,
(c) a second protein, wherein the second protein is attached to the first protein via biotin-streptavidin interactions and is modified to bind a ligand,
(d) a ligand that binds the second protein and is modified so that it attaches to the second electrode, thereby forming an electronic contact between the first and second electrodes and the first and second protein.

19. The bioelectronic circuit according to the above 18, wherein the first protein comprises two biotins.

20. The bioelectronic circuit of the above 19, wherein the second protein comprises two biotinylated Avitag sequences.

21. A bioelectronic circuit comprising:
(a) a first and a second electrode,
(b) a first and a second protein, wherein one of, or both, the first and the second proteins are attached to the first and second electrodes through biotin-streptavidin interactions, thereby forming an electronic contact between the first and the second electrodes and one of, or both, the first and the second proteins.

22. The bioelectronic circuit of the above 21, wherein the first binding site comprises one or more residues that can be biotinylated.

23. A bioelectronic circuit comprising:
(a) a first and a second electrode,
(b) a first protein, wherein the first protein is attached to the first electrode via biotin-streptavidin interactions,
(c) a second protein, wherein the second protein is attached to the first protein via biotin-streptavidin interactions and is attached to the second electrode via biotin-streptavidin interactions,
(d) a third protein, wherein the third protein is attached to the first and the second proteins via biotin-streptavidin interactions, thereby forming an electronic contact between the first and second electrodes and the first, second and third proteins.

24. A bioelectronic circuit comprising:
(a) a first electrode,
(b) a first protein, wherein the first protein is attached to the first electrode via biotin-streptavidin interactions,
(c) a second protein, wherein the second protein is attached to the first protein via biotin-streptavidin interactions and is attached to the second electrode via biotin-streptavidin interactions,
(d) a second electrode in contact with an electrolyte and connected to the first electrode,
(e) a means for applying a voltage bias,
(f) a means for sensing current, thereby forming an electronic contact between the first and second electrodes and the first and second proteins.

25. A method of preparing a bioelectronic circuit, the method comprising:
(a) attaching at least one streptavidin molecule to at least one electrode,
(b) introducing a biotinylated protein to the streptavidin-electrode from step (a) to form a complex comprising the at least one electrode, the at least one streptavidin molecule and the biotinylated protein.

26. A method for detecting the activity of a polymerase, the method comprising introducing a solution of DNA template and nucleotriphosphates to the bioelectronic circuit of the above 4, wherein polymerized product indicates that the polymerase is active.

27. A method for detecting the activity of protein, the method comprising introducing a substrate of the protein to the bioelectronic circuit of the above 4 and detecting electrical changes.

28. A system for electrical measurement of protein activity comprising:
(a) a bioelectronic circuit as herein described,
(b) a means for applying a bias between the first and second electrode, and
(c) a means for detecting the current through the bioelectronic circuit.

29. A bioelectronic circuit as herein described wherein the protein comprises two or more Avitag sequences placed at the surface of the protein and no more than 10 amino acid residues from tyrosines, tryptophans or histidines within the protein.

30. A bioelectronic circuit comprising:
(a) a first and a second electrode,
(b) a first and a second ligand that are specific for a protein, wherein the ligands are modified so that the first ligand attaches to the first electrode and the second ligand attaches to the second electrode,
(c) a first protein and a second protein that bind the first ligand and the second ligand, and
(d) a third protein that is modified to bind the first and the second proteins, wherein the binding of the third protein to the first and the second proteins forms an electronic contact between the electrode and the protein.

31. The bioelectronic circuit of the above 30, wherein the first and second proteins are streptavidin 32. The bioelectronic circuit of the above 30, wherein the first and second ligands are biotin.

33. The bioelectronic circuit of the above 30, wherein the third protein is biotinylated.

34. A bioelectronic circuit comprising:
(a) a first and a second electrode,
(b) a first and a second ligand that are specific for a protein, wherein the ligands are modified so that the first ligand attaches to the first electrode and the second ligand attaches to the second electrode, and
(c) at least a first protein and a second protein that bind the first ligand and the second ligand, and may be coupled to further proteins via ligands, extending the range over which conduction is obtained.

Definitions

Unless defined otherwise, all technical and scientific terms used herein have the same meaning as those commonly understood by one of ordinary skill in the art to which this invention belongs. Although methods and materials similar or equivalent to those described herein can be used in the practice or testing of the present disclosure, suitable methods and materials are described below. The materials, methods and examples are illustrative only, and are not intended to be limiting. All publications, patents and other documents mentioned herein are incorporated by reference in their entirety.

Throughout this specification, the word "comprise" or variations such as "comprises" or "comprising" will be understood to imply the inclusion of a stated integer or groups of integers but not the exclusion of any other integer or group of integers.

The term "a" or "an" may mean more than one of an item.

The terms "and" and "or" may refer to either the conjunctive or disjunctive and mean "and/or".

The term "about" means within plus or minus 10% of a stated value. For example, "about 100" would refer to any number between 90 and 110.

Biolectronic Circuits

The present disclosure provides a bioelectronic circuit. The bioelectronic circuit comprises (a) at least one electrode, (b) at least one ligand that is specific for a protein, wherein said ligand is modified so that it attaches to the at least one electrode, and (c) at least one protein that binds the at least one ligand, thereby forming an electronic contact between the electrode and the protein.

Depending on the application, the bioelectronic circuit comprises one or two electrodes in direct contact with proteins. In the case where only one electrode is in contact with the proteins, the circuit is completed by means of ion currents that flow between a redox-active protein and a remote electrode. In one embodiment, the bioelectronic circuit comprises one electrode. In another embodiment, bioelectronic circuit comprises two electrodes. In some aspects of this embodiment, the second electrode is not separated from the first electrode by an electrolyte.

The at least one electrode comprises a noble metal. In one embodiment, the at least one electrode comprises a noble metal selected from the group consisting of palladium, gold, and platinum. In another embodiment, the at least one electrode is palladium. In another embodiment, the at least one electrode is gold. In another embodiment, the at least one electrode is platinum. In addition to the at least one electrode, the bioelectronic circuit comprises a ligand that is specific for a protein and is modified so that it attaches to the at least one electrode.

The ligand can be modified to contain a thiol termination at one end for coupling to metals, as described by Zhang et al.[5] Examples of ligands are peptide epitopes for antibodies comprising a cysteine residue at one end, recognition peptides (such as the RGD peptide for binding integrin comprising a cysteine) and small molecules to which proteins have been selected to bind (such as an IgE molecule that binds dintitrophenyl and comprising a thiol).

Exemplary ligands that are specific for a protein and modified to attach to an electrode include, but are not limited to, $HSCH_2CH_2$-dinitrophenol (target protein IgE Anti-DNP), CALDRWEKIRLR (target protein IgG Anti-HIV) (SEQ ID NO: 1), CHNTPVYKLDISEATQV (target protein IgG Anti-Ebola) (SEQ ID NO: 2), CHNTPVYKLDISEATQV (target protein Fab Anti-Ebola) (SEQ ID NO: 2), cyclic RGDfC (target protein $\alpha_V\beta_3$ Integrin), thiolated-streptavidin (target Biotin), and $HSCH_2CH_2$-biotin (target Streptavidin). A summary of these various binding arrangements is given in Table 1 below, adapted from Zhang et al.[5]

TABLE 1

| Target | MW (kD) | Height (nm) | Probe on electrodes | $K_D$ (nM) | Control | Peak Conductance (nS) | Binding Mode |
|---|---|---|---|---|---|---|---|
| IgE Anti-DNP | 190 | ~5[1] | $HSCH_2CH_2$-dinitrophenol | 65 | IgE isotype | 0.27 ± 0.03, 1.96 ± 0.47 | NS-S S-S |
| IgG Anti-HIV | 150 | ~7[2] | CALDRWEKIRLR (SEQ ID NO: 1) | 240 | IgG isotype | 0.33 ± 0.03, 2.18 ± 0.36 | NS-S S-S |
| IgG Anti-Ebola | 175 | ~7[2] | CHNTPVYKLDISEATQV (SEQ ID NO: 2) | 1400 | IgG isotype | 0.26 ± 0.007, 2.09 ± 0.09 | NS-S S-S |
| Fab Anti-Ebola | 50 | ~7[3] | CHNTPVYKLDISEATQV | NA | IgG isotype | 0.30 ± 0.008 | NS-S |

TABLE 1-continued

| Target | MW (kD) | Height (nm) | Probe on electrodes | $K_D$ (nM) | Control | Peak Conductance (nS) | Binding Mode |
|---|---|---|---|---|---|---|---|
| $a_r\beta_3$ Integrin | 190 | ~10[4] | Cyclic RGDfC | ~10 | $a_4b_1$ Integrin | 0.38 ± 0.009 | NS-S |
| Biotin | NA | NA | Thiolated-streptavidin | ~10$^{-5}$ | NA | 0.35 ± 0.008 | T-T |
| Streptavidin | 55 | ~3.5[5] | HSCH$_2$CH$_2$-biotin | ~10$^{-5}$ | NA | 0.26 ± 0.01, 1.48 ± 0.07, 6.80 ± 0.6 | S-S |

Proteins and ligands used in this study. The cysteine or thiol used for electrode attachment is in bold.
Linear dimensions are from the RSCB PDB, either across a minor diameter or, for the antibodies, binding head to binding head:
[1] IgE structure 4GRG,
[2] IgG, structure 4NHH, Fab fragment structure 1YUH,
[4] Integrin structure 1L5G,
[5] streptavidin structure 1VWA.

The bioelectronic circuit also comprises at least one protein that binds the at least one ligand. The protein can be any protein that can be expressed in a medium that allows for modification of the native protein sequence. Thus, any protein function can be incorporated into an electrical circuit so that changes induced by ligand or substrate binding, or enzyme activity can then be measured electrically.

In one embodiment, the bioelectronic circuit comprises (a) two palladium electrodes, (b) thiolated streptavidin attached to the palladium electrode, and (c) biotinylated polymerase, thereby forming an electronic contact between the electrode and the polymerase. It should be understood that while the bioelectronic circuit described below comprises palladium electrodes, thioloated streptavidin, and a biotinylated polymerase, this embodiment is illustrative of the present disclosure and the scope of the present disclosure is not limited to this one embodiment.

In one aspect of this embodiment, thiolated streptavidin with an average of 2.5 thiols per tetramer was obtained from ProteinMods (Madison, Wisconsin). The streptavidin (31 in FIG. 3) was incubated in a 1 μM aqueous solution with a pair of noble metal (palladium) electrodes (the pair forming a nano-scale junction approximately 5 nm gap, 32, 33 in FIG. 3). Incubation overnight produced a dense coating of the streptavidin attached to the metal electrodes by means of a surface thiol (34).

Figure 3:
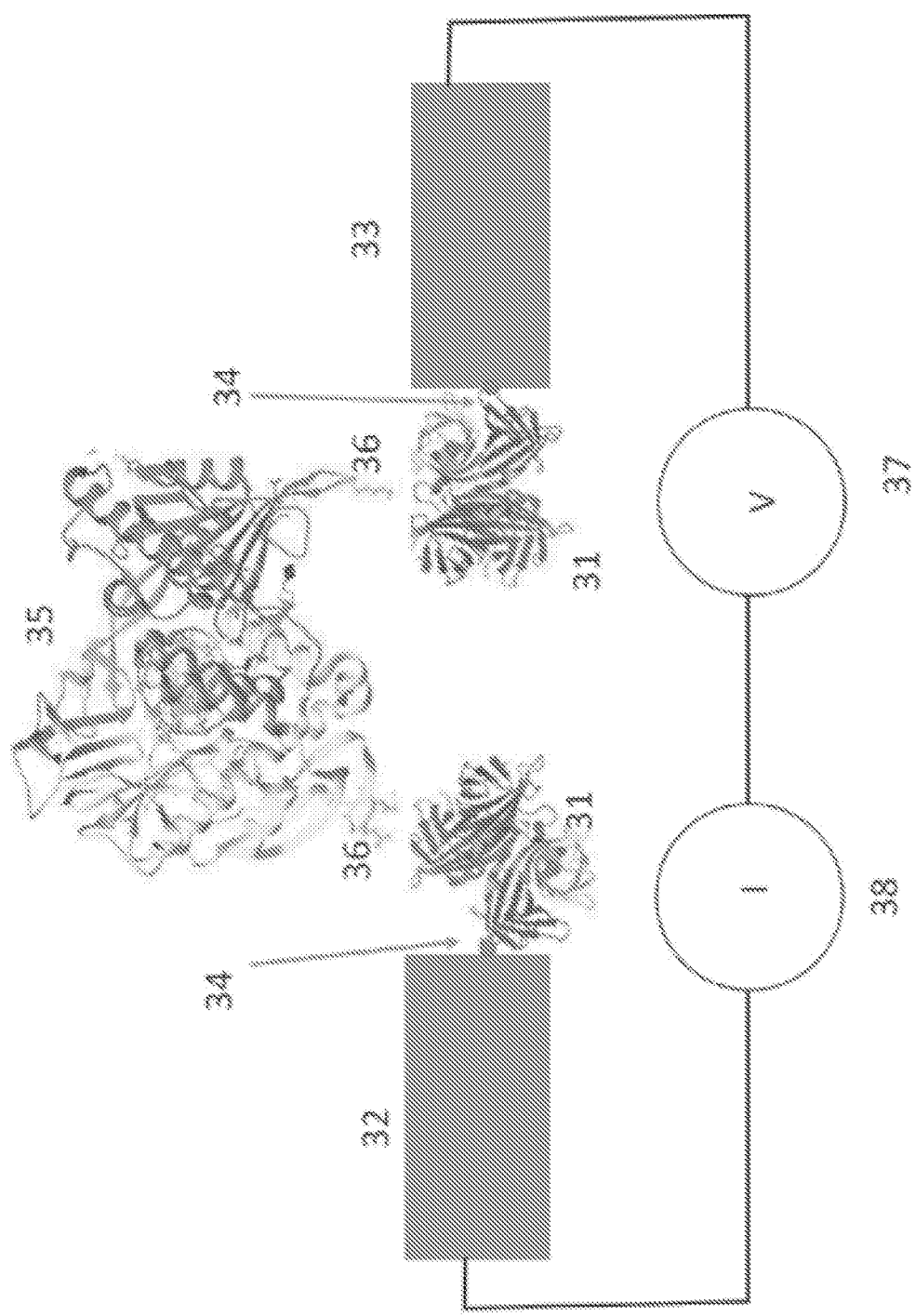
FIG. 3 shows a schematic diagram of a bioelectronic circuit using streptavidin wires to wire a biotin-modified polymerase into the circuit.

In order to complete the bioelectronic circuit, a bis-biotinylated φ29 polymerase was constructed (35 in FIG. 3). The Avitag peptide sequence, GLNDIFEAQKIEWHE (SEQ ID NO: 4), was inserted between residues G111 and K112, and a second Avitag peptide sequence was inserted between E279 and D280 in the φ29 polymerase sequence (the exonuclease activity of which was deleted by mutating D12 and E14 to alanine). This produced a polymerase with two Avitags separated by about 5 nm. The Avitags were biotinylated using the BirA enzyme, as is well known in the art. The resulting molecule (35) therefore contained two biotin molecules (36 in FIG. 3). The biotinylated polymerase was incubated with the streptavidin functionalized junction for two hours (in 1 μM aqueous solution of φ29 polymerase). The electrical properties of the bioelectronic circuit were measured by applying a voltage bias V across it (37) and recording the current (38) through the circuit. As noted by Zhang et al.,[5] this bias must be less than 100 mV to avoid contact-generated noise, and 50 mV bias was used to collect the data shown here.

Figure 4:
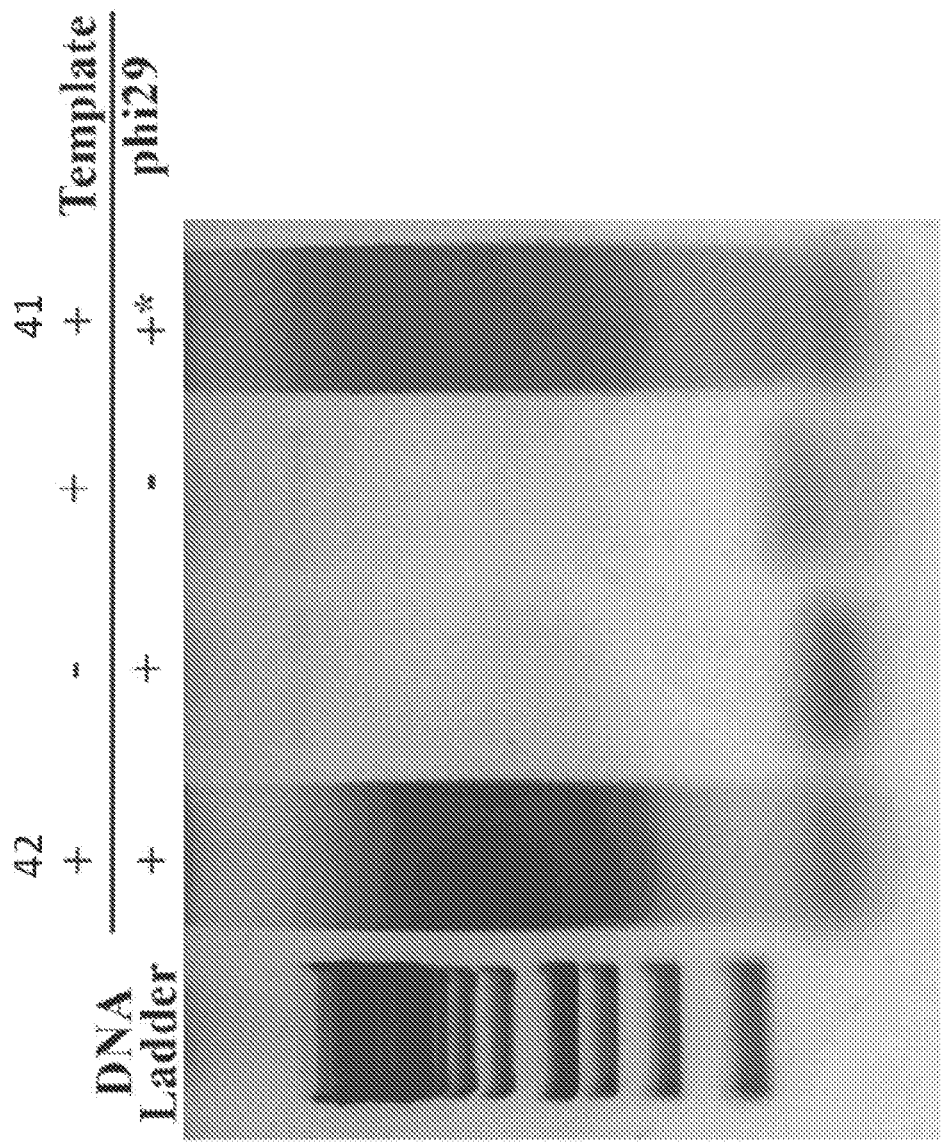
FIG. 4 shows a gel assay demonstrating that biotinylated polymerase bound to two streptavidin molecules is active and capable of efficient enzyme action.

To confirm that the modified polymerase was still active, rolling-circle amplification of a DNA template was carried out with the molecule 35 as bound by two streptavidin molecules. The polymerase activity, as monitored by a DNA gel of the polymerization product (42 in FIG. 4) is comparable to that of the native enzyme with exonuclease activity deleted (41 in FIG. 4).

In order to confirm that the bis-biotinylated molecule 35 bridged the junction, a monobiotinylated φ29 polymerase was prepared. To do this, the following sequence was added to the N-terminus of the WT (but exonuclease inactivated) enzyme: MGSSHHHHHHSSGLVPRGSGLNDIFEAQK-IEWHEGASS (SEQ ID NO: 5), in which five histidines are a his-tag for purification of the protein and GLNDIFEAQK-IEWHE (SEQ ID NO: 4) is the Avitag.

Figure 5A:
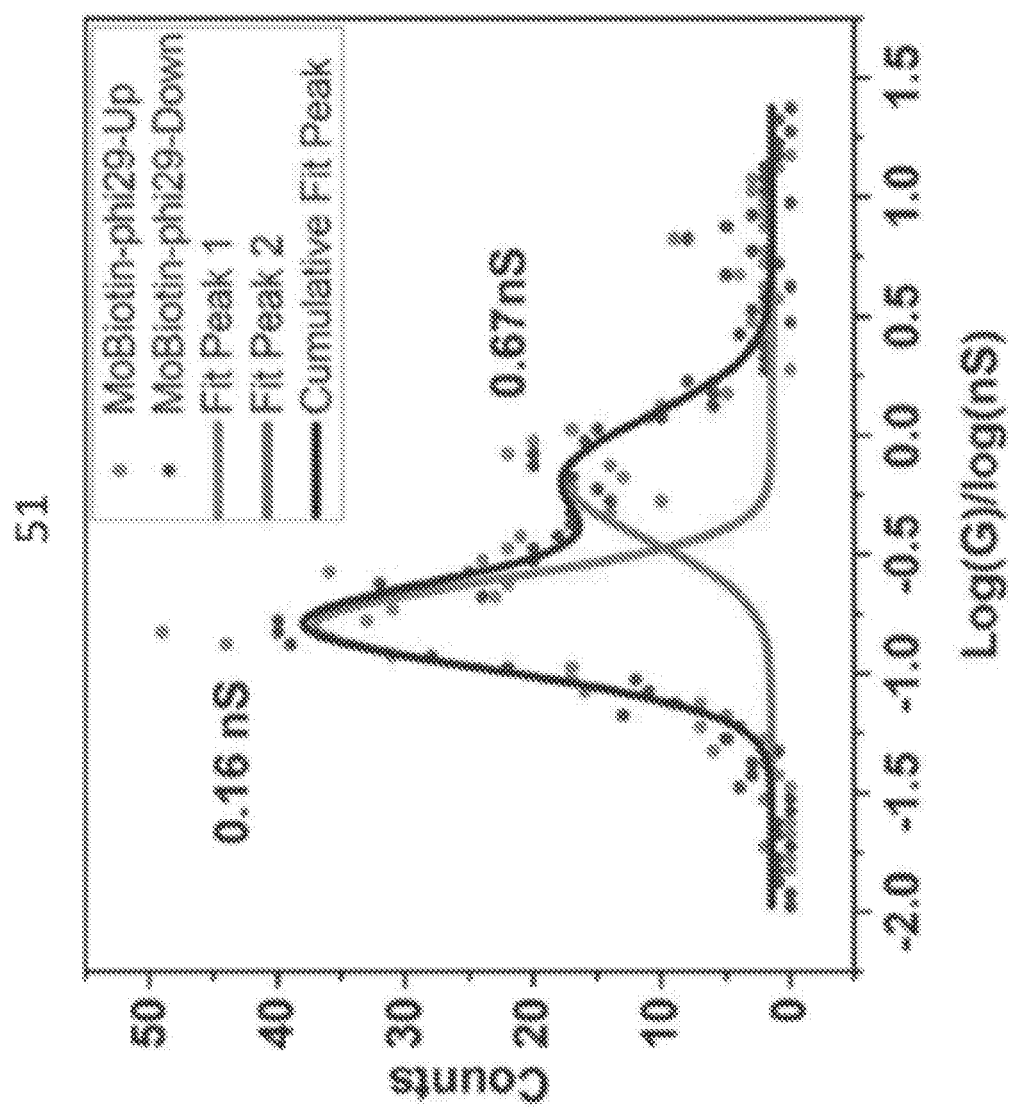
FIG. 5A and FIG. 5B show a comparison of the measured conductance distributions for mono-biotinylated and bis-biotinylated polymerases.
Figure 5B:
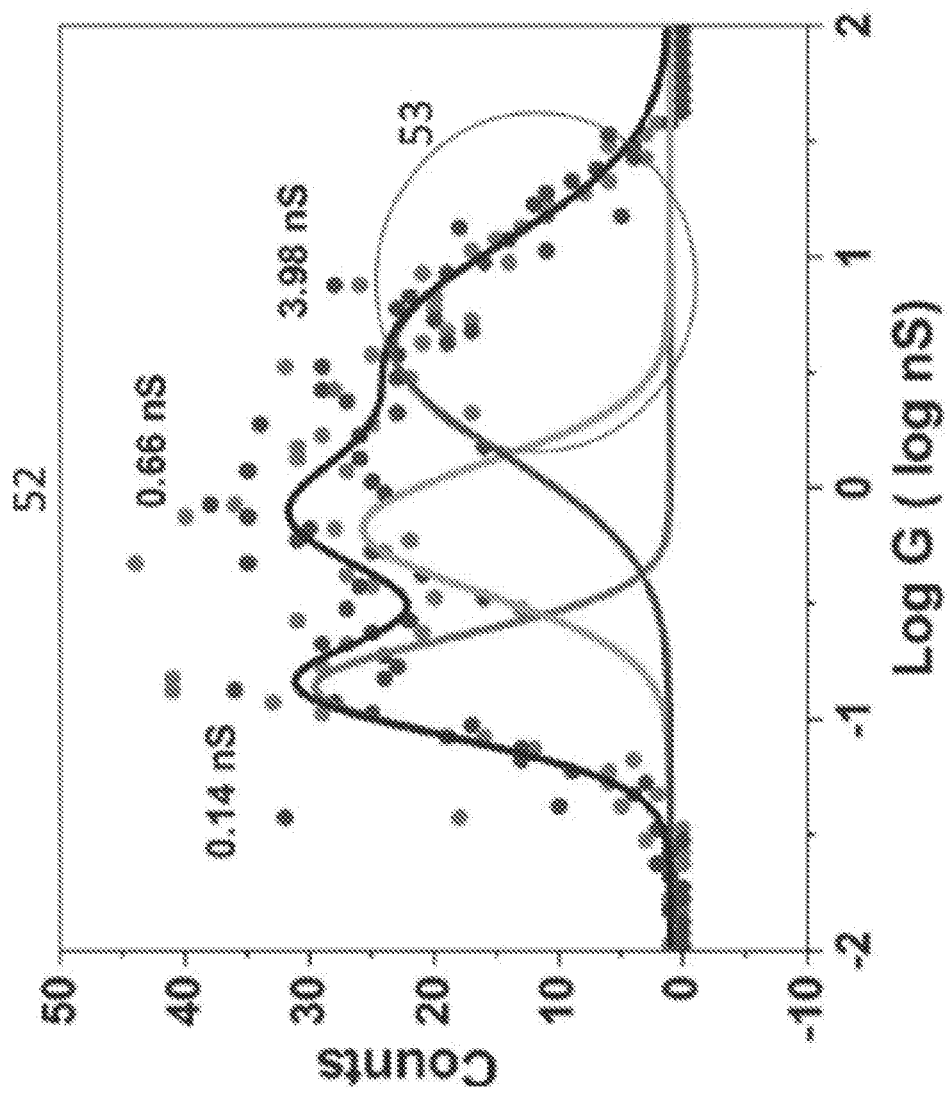

In order to characterize the conductance of the molecular circuits in all its possible binding geometries, repeated measurements were made on different molecular junctions, and the frequency with which particular values of conductance are recorded on a logarithmic conductance scale were plotted (as described in Zhang et al.[5]). FIG. 5 shows such distributions for the mono-biotinylated polymerase (51) and the bis-biotinylated polymerase (52). The bis-biotinylated molecule shows a new, high conductance feature (53) not present in the distribution measured for the mono-biotinylated molecule. This feature corresponds to about 4 nS conductance, a substantial increase over the highest conductance feature observed for the mono-biotinylated molecule (about 0.7 nS). This is a similar increase to that observed for molecules like antibodies connected by one or two specific contacts, as described by Zhang et al.[5] Note that these very high conductivities are obtained with the streptavidin molecules forming part of the circuit, showing that assemblies of several proteins in sequence maintain their quasi-metallic properties if they are properly connected.

Figure 6A:
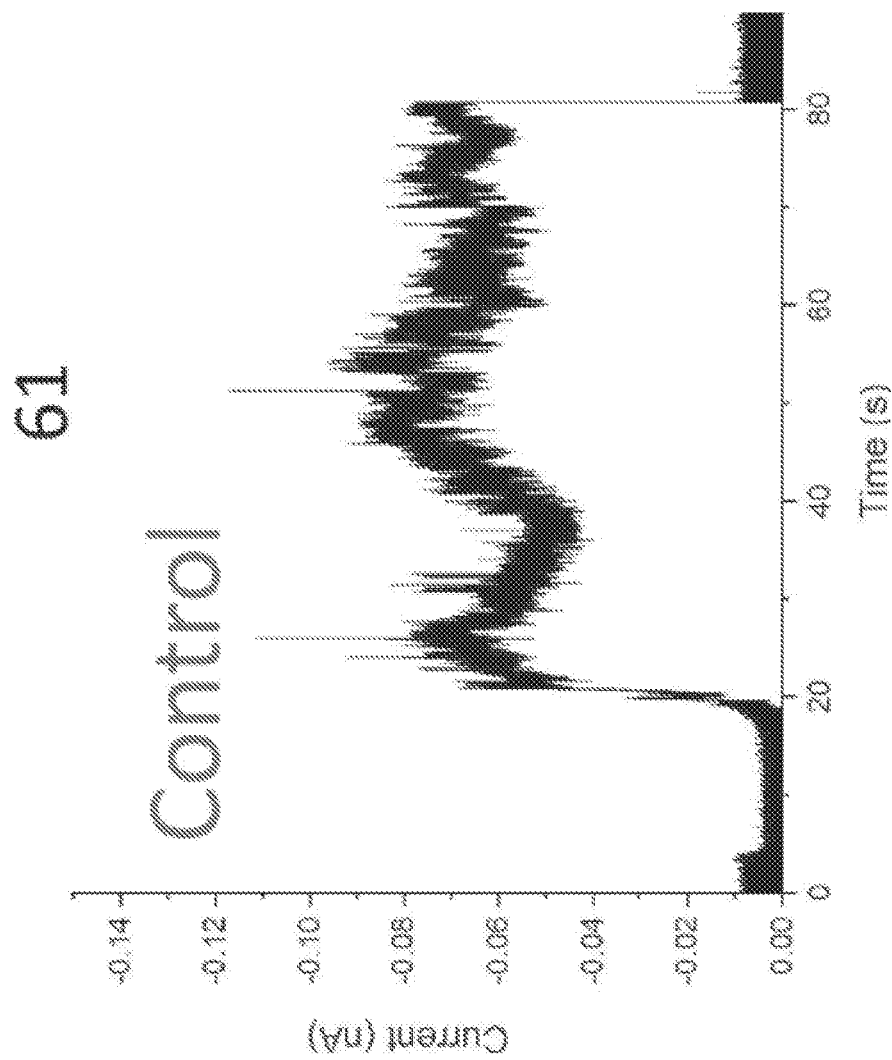
FIG. 6A and FIG. 6B show a recording of current vs time for a polymerase molecule wired into a bioelectronic circuit with streptavidin.
Figure 6B:
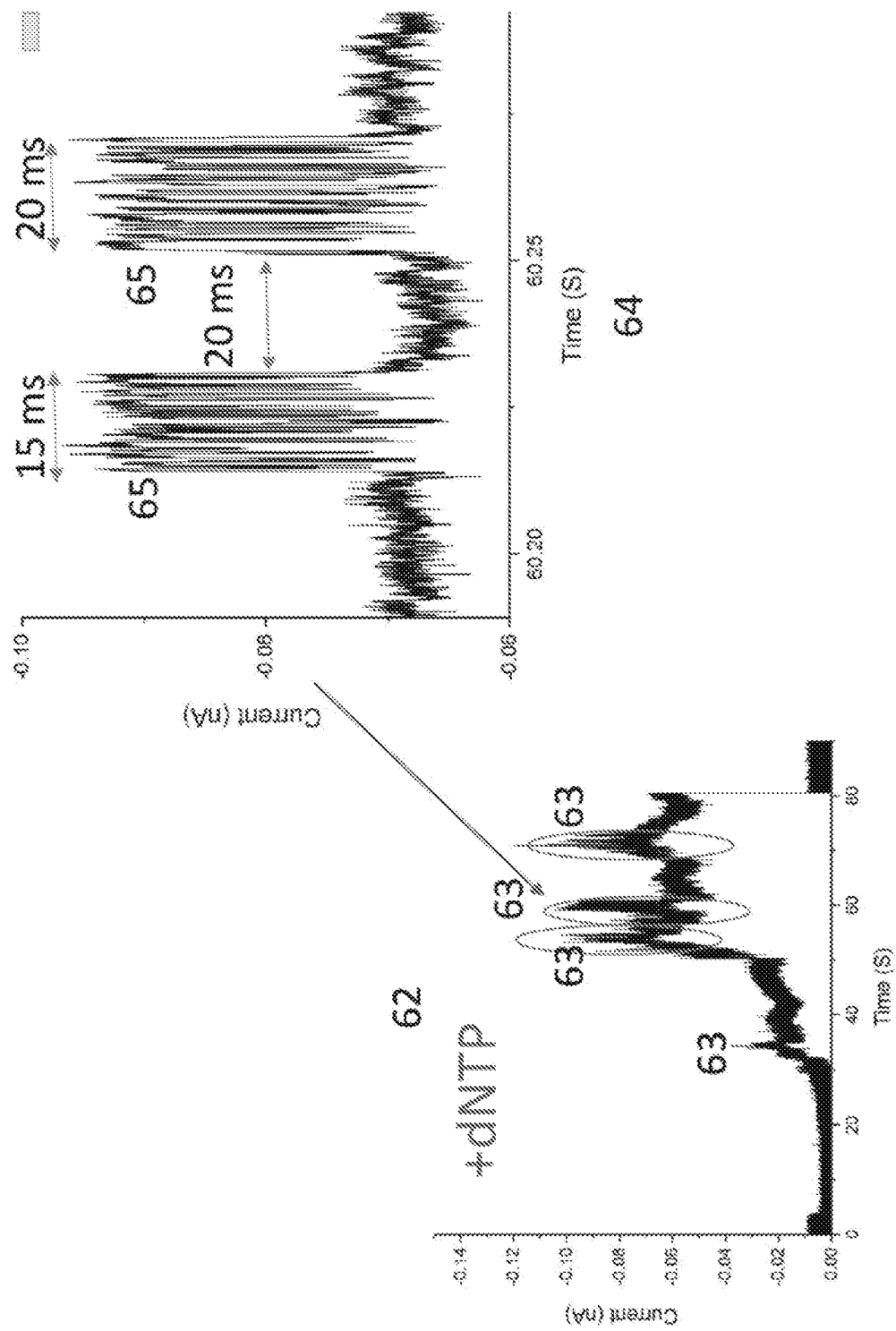

FIG. 6 shows electrical signals obtained from a bis-biotinylated polymerase molecule in its resting state 61 and its active state 62 where it is actively polymerizing a DNA template in the presence of dNTPs and Mg. In each case, current data were recorded for about 90 s after an electrode was moved into contact with the complex. Formation of the streptavidin-φ29 polymerase contact takes about 20 s, after which the current (at 50 mV bias) jumps from zero to about 60 pA. In the case of the control molecule 61 the current remains fairly quiet and constant for the remainder of the run. For the active molecule 62, bursts of noise 63 are observed, each lasting for a few seconds. A 50 ms portion of one of these bursts is also shown (64)—the bursts themselves consist of sub-bursts (65), the duration and spacing of which are consistent with the interpretation that each sub-burst (65) signals the incorporation of a single nucleotide (given the known kinetics of φ29 polymerase). This illustrates the use of the current invention in building circuits that can monitor enzyme activity electrically.

Recognizing the importance of placing a contact as close to the hydrophobic interior of a protein as possible, while still having the contact point itself appear on the surface of the protein, sites for insertion of the Avitags should be placed as close aromatic residues as possible while still exposing the site for biotinylation at the exterior of the protein. Therefore, the Avitag should be placed as close as possible to tyrosines, tryptophans or histidines that are near the surface of the protein.

In a second embodiment, the bioelectronic circuit comprises (a) two palladium electrodes, (b) thiolated biotin attached to the palladium electrode, and (c) streptavidin. This embodiment allows for a uniform coating of small molecules on the electrode.

Figure 2:
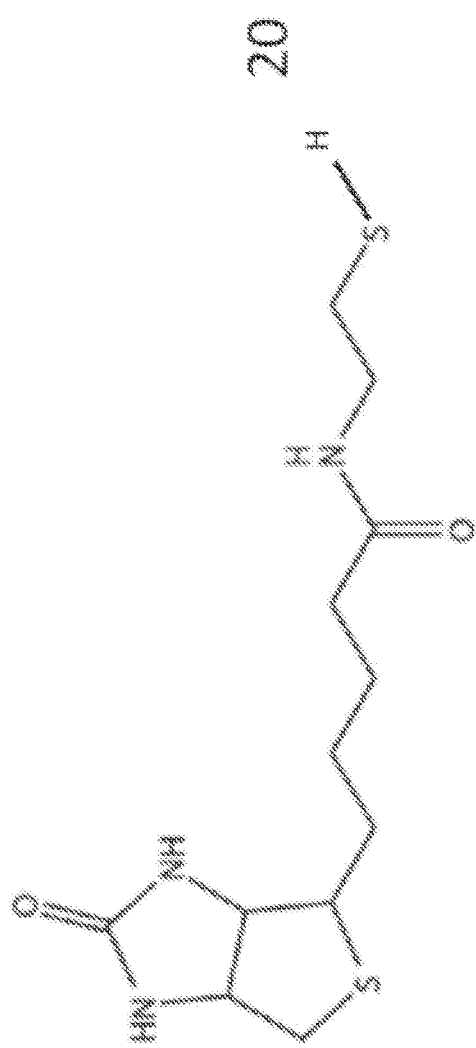
FIG. 2 shows the chemical structure of the reduced version of the molecule shown in FIG. 1.

In one aspect of this embodiment, biotinylated cystamine was used as the thiolated biotin. N,N'-bisbiotinyl-cystamine 11 (chemical structure shown in FIG. 1) was synthesized as described in the Examples. Because of the S-S linkage (12 in FIG. 1), 11 is stable in oxidizing environments (like air). It can be reduced to the monothiol 20 (chemical shown in FIG. 2) in the presence of a strong reducing agent. Reducing agents are known in the art and any can be used. In some embodiments, the reducing agent is an immobilized TCEP (Tris[2-carboxyethyl] phosphine hydrochloride) disulfide reducing gel from Thermo Scientific (cat #77712).

In this second embodiment, electrodes are functionalized with thio-biotin, and the junction is then exposed to wild type (i.e., lacking surface thiols) streptavidin. The result is a strongly conducting bridge. This is illustrated in FIG. 7. In a control experiment (71) the gap is bridged by a thiolated streptavidin molecule which has been incubated with biotin (this is because biotin binding changes the conductance of streptavidin as described by Zhang et al.[5] so it is necessary to compare biotin-bound streptavidin molecules to see the intrinsic contact differences in these experiments). In the second measurement (72) the electrodes are first functionalized with the mono-thiolated biotin (20) and then wild type streptavidin is introduced to bind and complete the circuit. The current distribution for the thiolated streptavidin (as biotin bound) directly attached to the electrodes is shown in 73. The distribution for the wild type streptavidin captured between biotinylated electrodes is shown in 74. A new, high conductance feature is observed at nearly 7 nS (75) in the case where the thio-biotin molecule (20) is used to attach the streptavidin to the electrodes. Remarkably, connection via a specifically-binding ligand (biotin) that is, itself, attached to the electrode via a thiol, can form a better contact than a direct attachment of the protein itself via a surface thiol on the protein.

In the embodiments described above, the protein contains one contact for a ligand. In the embodiments described in the following paragraph, the protein contains a second contact for a ligand.

For example, the integrin molecule listed in Table 1 has one binding site for a small ligand that makes an excellent electrical contact (the cyclic RGD peptide incorporating a cysteine as listed in Table 1). But contact to a second point cannot be made via another ligand, because this integrin only has one RGD binding site. However, a well-defined circuit can be completed by incorporating an Avitag sequence into a region near the N terminus of the integrin, so that now it has two specific binding sites: (1) the RGD peptide binding site and (2) the biotin binding site. Heterogeneous contacts like this (peptide binding at one site, biotinylation at another) have the advantage that the protein can be oriented in an assembly by exploiting the selective attachment now incorporated into the protein. For example, one electrode might be functionalized with the streptavidin, and a second with the peptide (i.e., cyclic RGD), so that the modified protein would then always be bound in a well-defined orientation with respect to both electrodes. The same technology enables sequential assembly of protein circuits. This is illustrated with the protein "AND" gate shown in FIG. 8.

More specifically, with protein A (81) designed or chosen such that binding of ligand A causes an increase in conductivity and protein B (82) designed or chosen such that binding of ligand B causes an increase in conductivity, wired in series, and connected between electrodes, the pair comprise a chemical AND gate because the high conductance state is only obtained when both ligand A and ligand B are present. Clearly one way to guarantee that the proteins are wired in the desired order is the use of selective contacts. Thus, the first electrode, 84, is modified with the thio-biotin molecule 86 that binds a streptavidin molecule 87. This in turn binds protein A 81 that has been modified so as to have incorporated two biotinylated Avitag sequences 83. Further incubation with streptavidin places a second streptavidin 84 on protein A. At this point, protein B 82 can be bound using a biotinylated Avitag sequence 83. If the same biotin-streptavidin coupling were to be used to complete the circuit contact to the second electrode 85, the undesirable possibility arises that a protein A could become incorporated at the second position where a protein B is desired. In order to overcome this possibility, a heterogeneous linkage is used, in this case exploiting a peptide binding site 88 on protein B. The corresponding peptide ligand 89 bound to the second electrode 85 completes the circuit by binding to its cognate site on protein B. It will be recognized that additional useful building blocks can be created by linking one ligand to another. For example, by concatenating a peptide ligand (such as one of those shown in Table 1) to a biotin molecule, so that a first protein with a specific binding site to the peptide could be linked to streptavidin, for example, for subsequent incorporation into a circuit via the remaining unoccupied biotin binding sites on the streptavidin.

Another consideration that arises in connecting functional proteins into a circuit with two contact points is the possible disruption of function caused by the mechanical constraints imposed by tethering the protein at two points. While connection at one point leaves the protein free to move much as though it were in solution, a second attachment point, especially one chosen to be distant from the first (so as to sense protein motion) could clearly disrupt protein function. Thus, it is highly desirable to incorporate a flexible linker into the region where a second contact site is incorporated. This could, of course be at either one of the two contact sites.

Sequences of amino acids that form flexible linkers are well known in the art and examples are listed on the world wide web at bmrb.wisc.edu/referenc/choufas.shtml. When selecting a particular flexible linker, there are three important design considerations.

The first consideration is that the incorporated sequence should not consist of short repeats, as this complicates cloning. To illustrate this, consider the well-known flexible linker amino acid sequence: GGSGGSGGSGGS (SEQ ID NO: 6). The corresponding DNA template is shown in FIG.

Figure 9B:
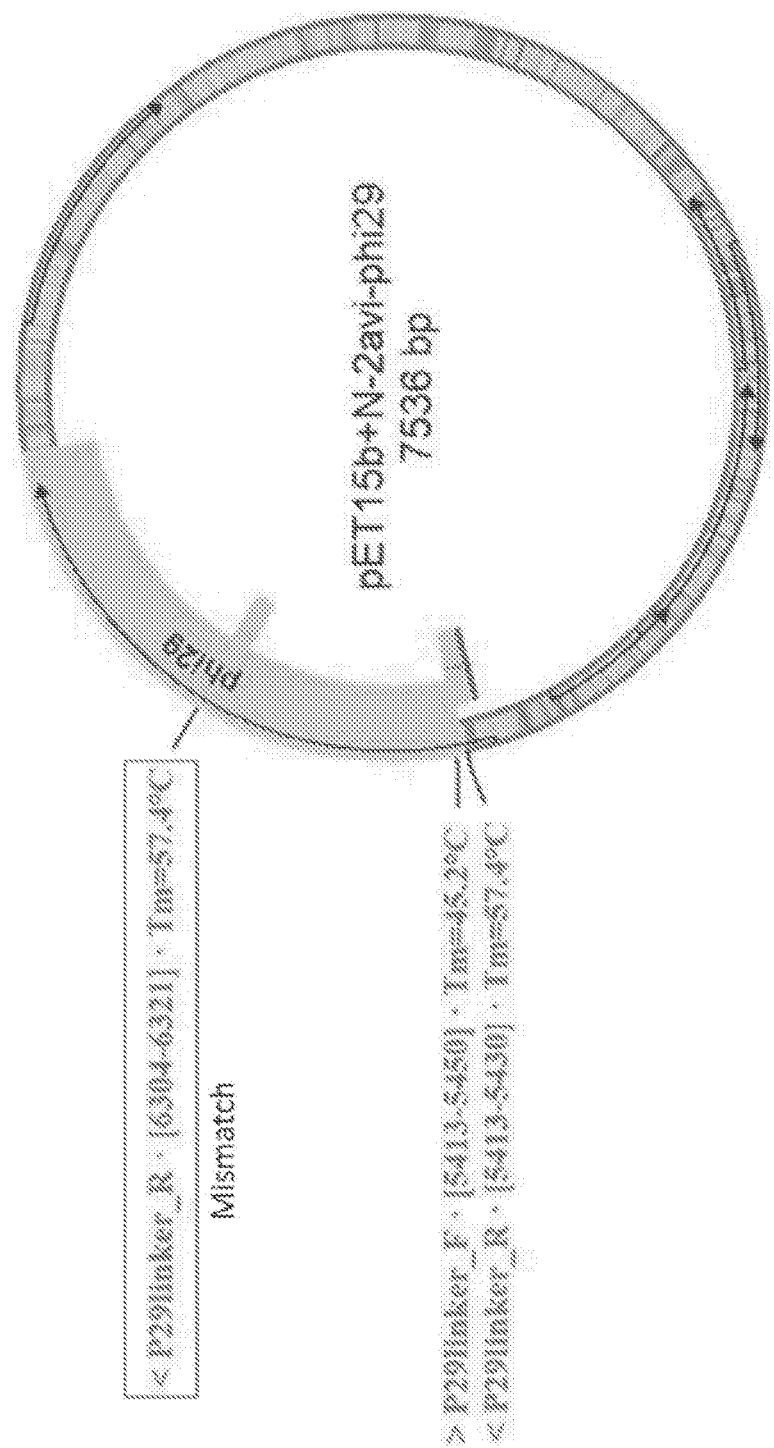

9A, which also shows the dimer that can be formed between primer sequences. The result, when cloned into an expression vector, is shown in FIG. 9B which shows the sequence of the resulting plasmid with the products of the undesired primer dimers labeled.

Figure 10B:
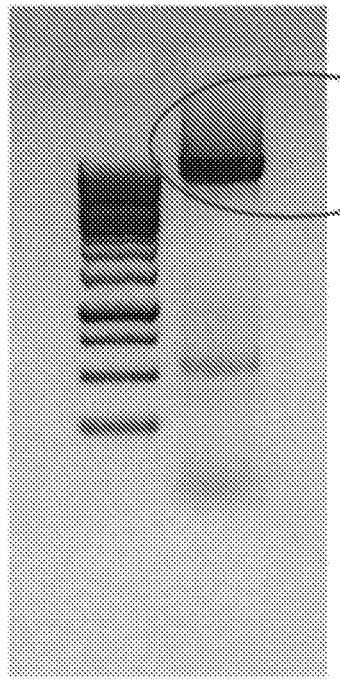

The second consideration is that the isoelectric point of the new protein should not be altered significantly, so that the residues in the inserted linker should be chosen to be neutral or nearly so. This is illustrated by the synthesis of a phi29 polymerase containing two Avitags for wiring into a circuit. In this case, the flexible linker was placed next to the Avitag sequence located near the N terminus. In the first case (sequence 101 in FIG. 10) the flexible linker (circled, 103) has the sequence GDSTDGTSDGSS (SEQ ID NO: 7) with the result that the protein product has a calculated pI of 7.25. This small shift from the pI of the native protein (which is a pI of about 8) is enough to cause misfolding resulting in the protein appearing as a shorter product 105 in a gel 106. When aspartic acid (D) is changed to asparagine (N) in the linker sequence (now GNSTNGTSNGSS (SEQ ID NO: 3)—104 in sequence 102) the native pI is restored (pI=8.13) and the product now runs at the position of the correctly folded native protein (107 in gel 108).

The third consideration arises when two identical sequences (i.e., two Avitag sequences) are to be inserted into the same clone expression system, as the corresponding repeated DNA sequence results in primer-dimers. To overcome this, the cloning proceeds in two steps. A clone with one Avitag sequence is first produced, and then a second clone is generated from this first clone with the second Avitag sequence inserted.

Figure 11A:
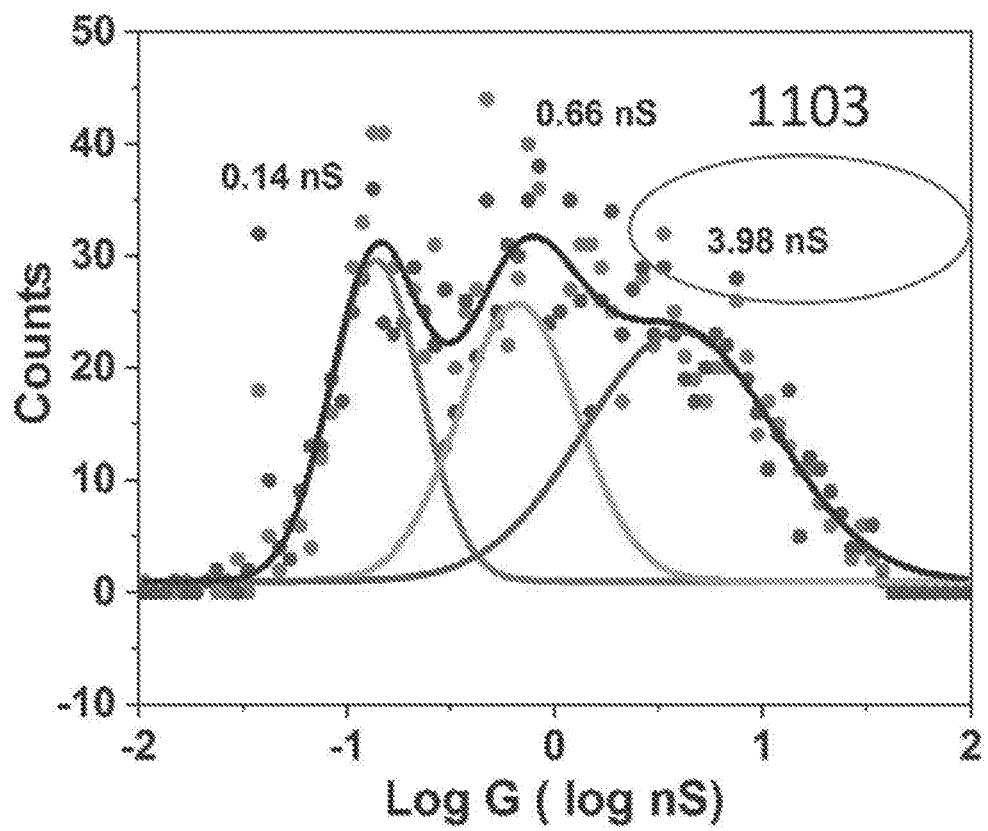
FIG. 11A and FIG. 11B show conductance distributions measured for two polymerases with and without a flexible linker sequence as wired into a circuit with biotin-streptavidin linkers.
Figure 11B:
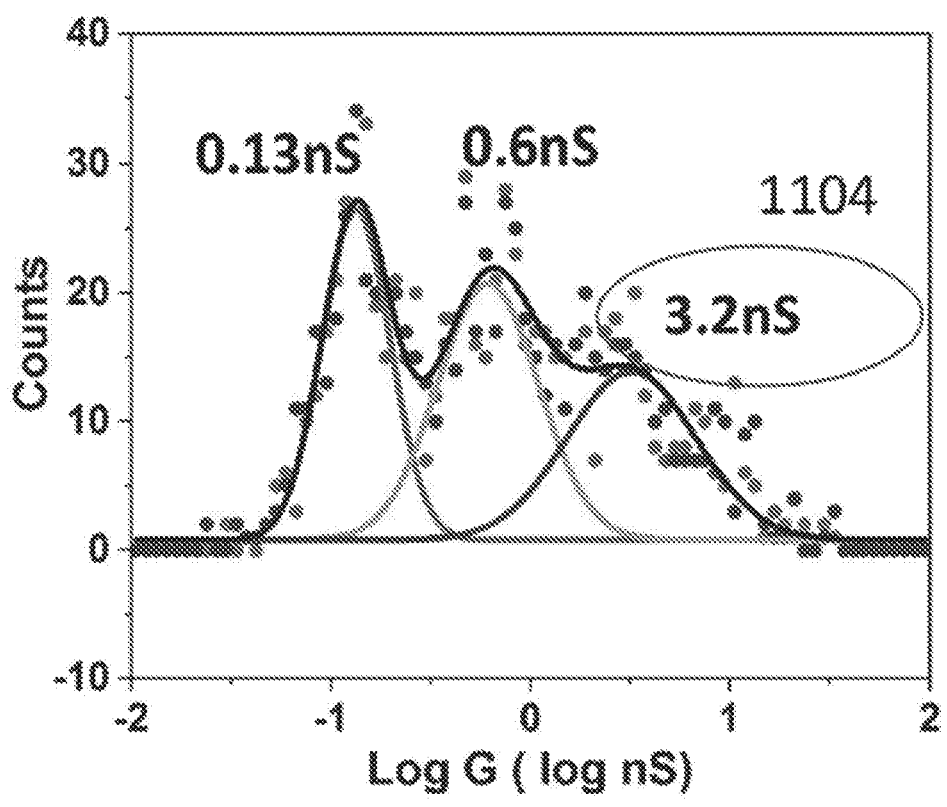

Given the flexibility of the GNSTNGTSNGSS (SEQ ID NO: 3) linker and the concern that a particular protein folding may be required to support this quasi-metallic state of the protein interior, a key question is whether the conductive properties of the protein are maintained when the linker is inserted. FIG. 11 shows the reference conductance distribution 1101 for the two-Avitag polymerase previously shown as 52 in FIG. 5 (lacking a flexible linker sequence). Here, the high conductance feature owing to binding the two biotinylated sites is labeled 1103. 1102 shows the conductance distribution for the phi29 incorporating a flexible linker (protein sequence 102 in FIG. 10). The high conductance feature is preserved (1104) showing that flexible peptide linkers can be incorporated while maintaining the quasi-metallic state of the protein.

Streptavidin is tetravalent (it binds up to four biotins) so, taken together with these remarkable and unexpected electronic properties, both of the coupling scheme and of the proteins themselves, completely new avenues for building bioelectronic circuits become available.

Figure 8:
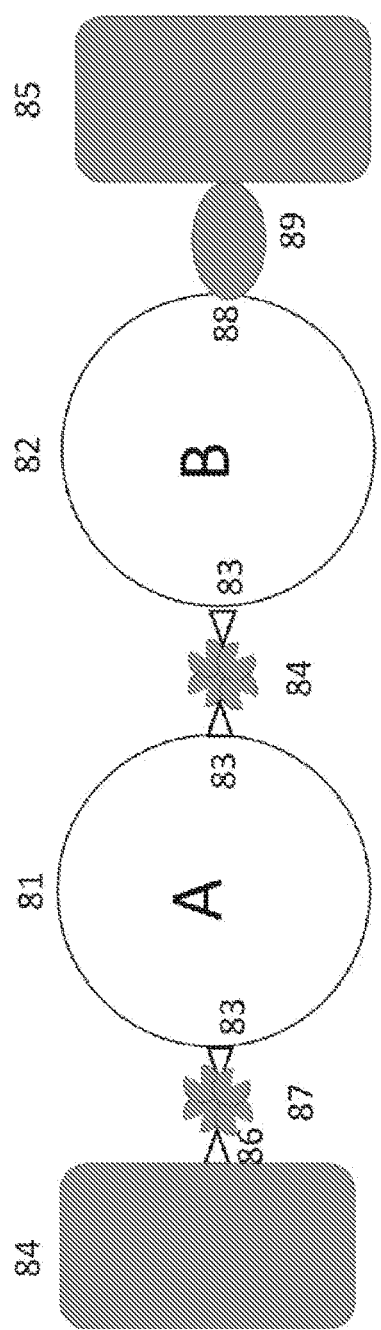
FIG. 8 shows a schematic diagram of orienting circuit elements using more than one selective ligand to form a biomolecular AND gate.
Figure 12:
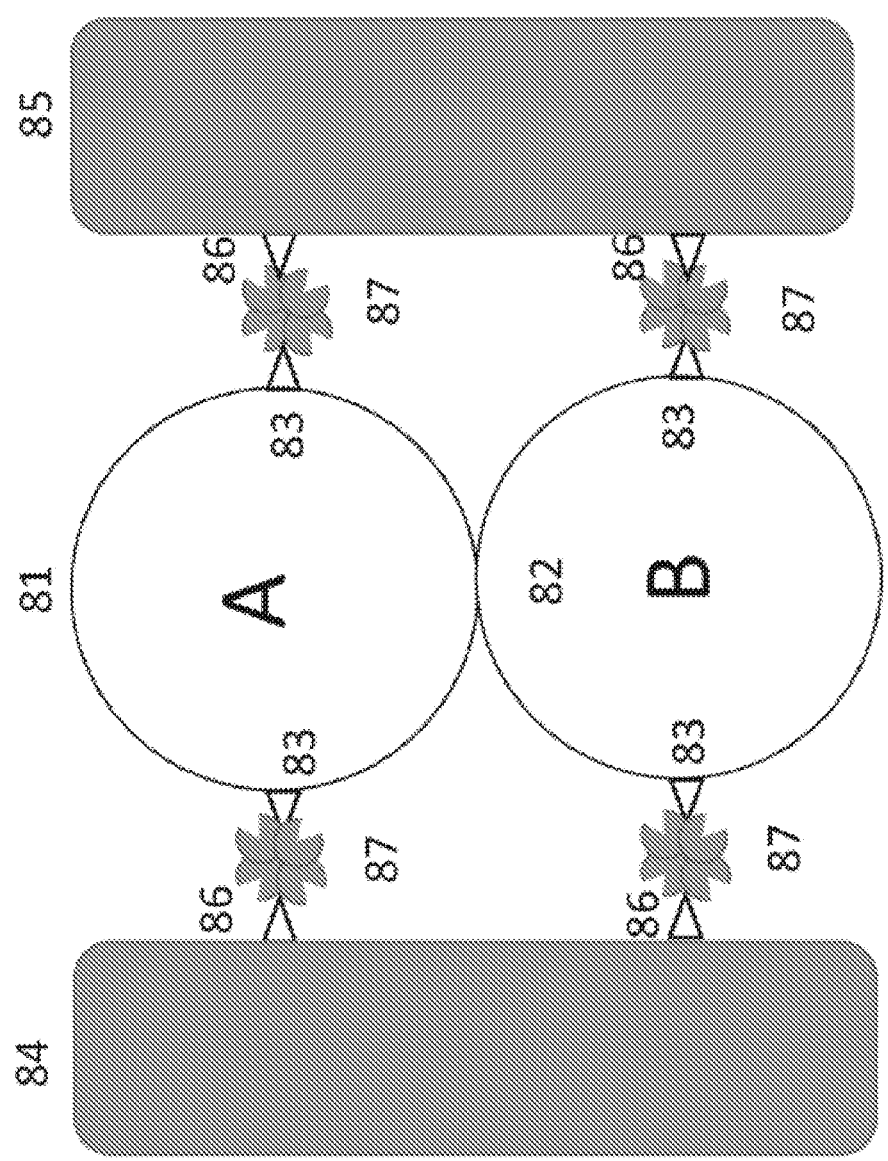
FIG. 12 shows a schematic diagram of a biomolecular OR gate.

FIG. 12 shows an "OR" gate based on the same assembly principles (the numbered components are as described for FIG. 8). This will enter the high conductance state if either ligand A or ligand B is present.

Figure 13:
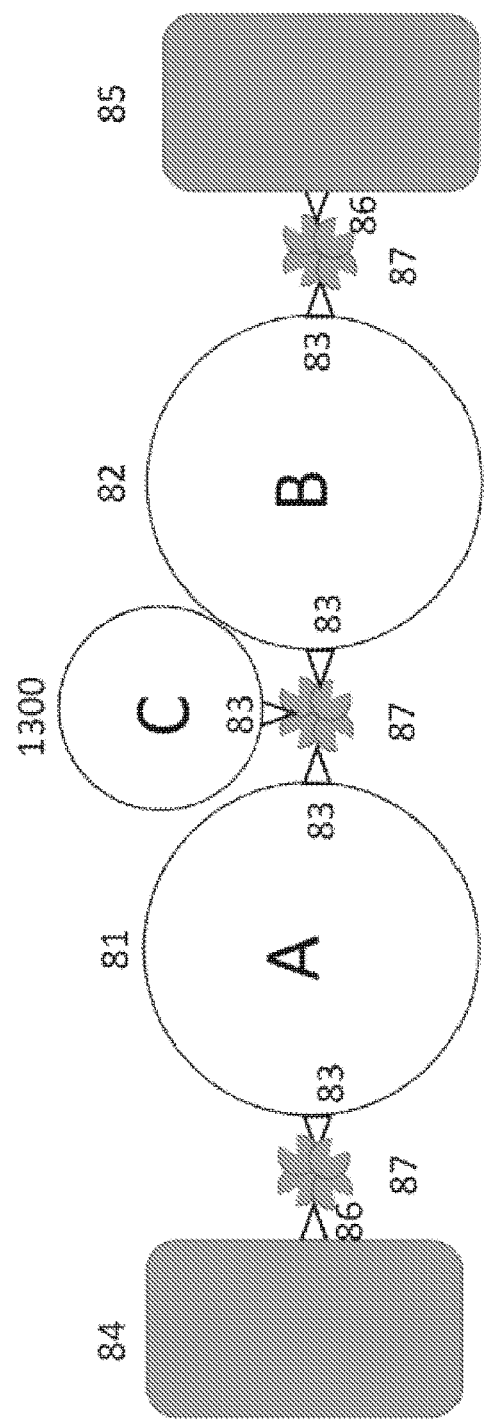
FIG. 13 shows a schematic diagram of a biomolecular three-state gate.

The tetravalent nature of streptavidin allows for even more complex circuits to be assembled. One version of this possibility is shown in FIG. 13 where, again, numbering is as in FIG. 8. Here, a third protein "C" (1300) is attached to the junction of protein A and protein B at an unoccupied site of the coupling streptavidin 87. If, for example, protein C is an electrochemically active protein that changes its oxidation state in the presence of oxidizing molecules, for example, then the change of charge on protein C will modulate electron transport through the A-B chain. Thus, the "A" AND "B" function can give rise to a third state that depends on the electronic state of "C".

Figure 14:
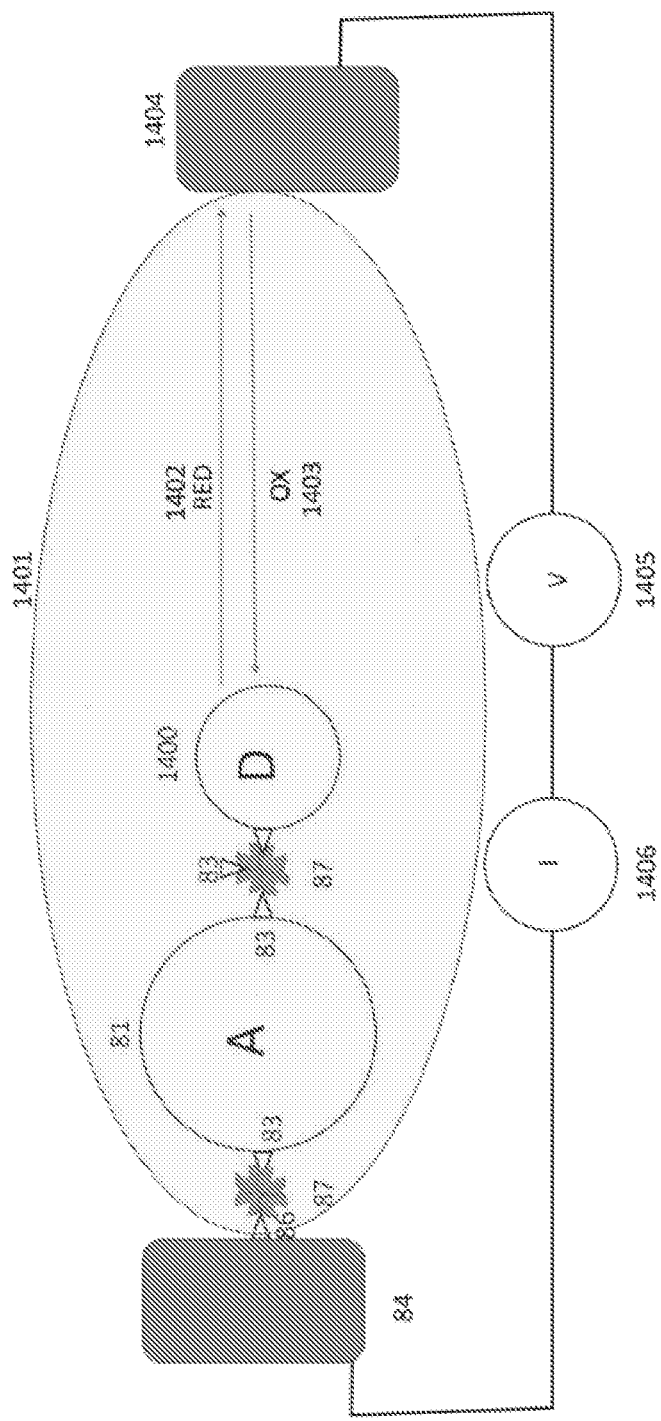
FIG. 14 shows a schematic diagram of a single electrode circuit in which the second contact is formed by a redox-active protein immersed in an electrolyte solution.

The embodiments described thus far have all utilized both a first and a second electrode. However, the quasi-metallic conductance of protein interiors, coupled with the ligand-based linkages described here would allow for very efficient electron transfer at the surface of a sensor electrode immersed in a solution containing molecules that generate redox activity in a sensor protein (for example, the glucose sensor). Thus, the protein or proteins of interest would be only linked directly to one electrode as illustrated in FIG. 14. Here, protein D 1400 is a redox active protein (for, example, glucose oxidase) immersed in an electrolyte 1401 containing a redox couple 1402, 1403 (for example, oxidized and reduced glucose) with a second (remote) electrode 1404 in contact with the electrolyte 1401 also, and connected to the first electrode 84 with a means for applying a voltage bias 1405 and a means for sensing the current 1406 that flows between the first electrode 84 and the second electrode 1404. This is an example of the use of the linkages of the present invention as applied to improve a currently existing electrochemical sensor technology.

Figure 15:
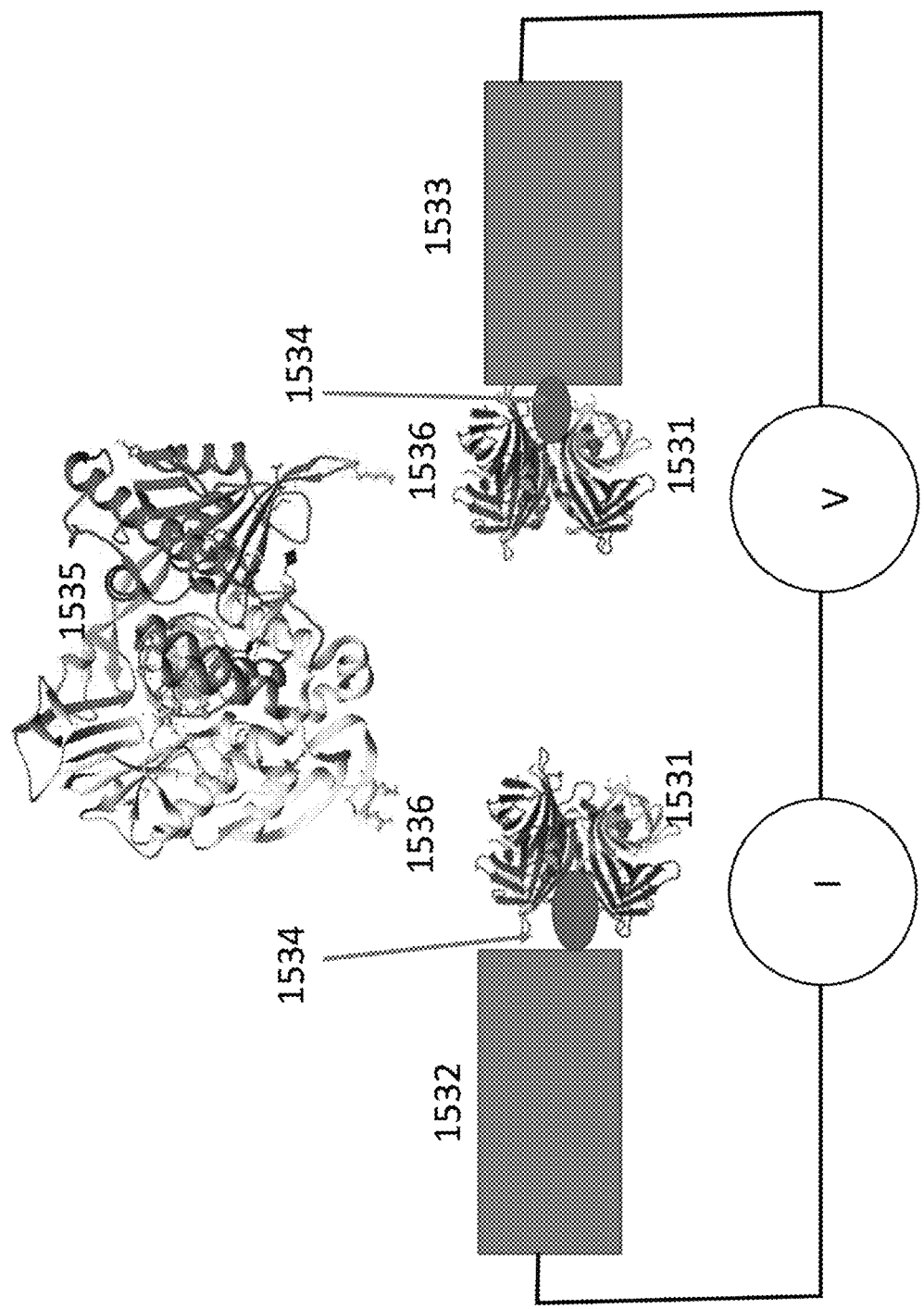
FIG. 15 shows a bioelectronic circuit in which an unmodified streptavidin is tethered to an electrode by the thio-biotin of FIG. 2

The bioelectronic circuit of FIG. 3 requires direct attachment of the modified coupling proteins to the electrodes. However, as shown in Zhang et al., coupling is more efficient if it is made via a small ligand attached to the electrode using an unmodified coupling protein. This has the advantage that the electrodes can be functionalized with a small ligand with which it is easier to obtain uniform coverage. Accordingly, FIG. 15 shows a first electrode 1532 modified with the thiobiotin of FIG. 2 1534 binding and unmodified streptavidin 1531 that in turn binds the protein 1535 that has been biotinylated at the tow sites 1536. Similar functionalization completes the coupling to the second electrode 1533.

Figure 16:
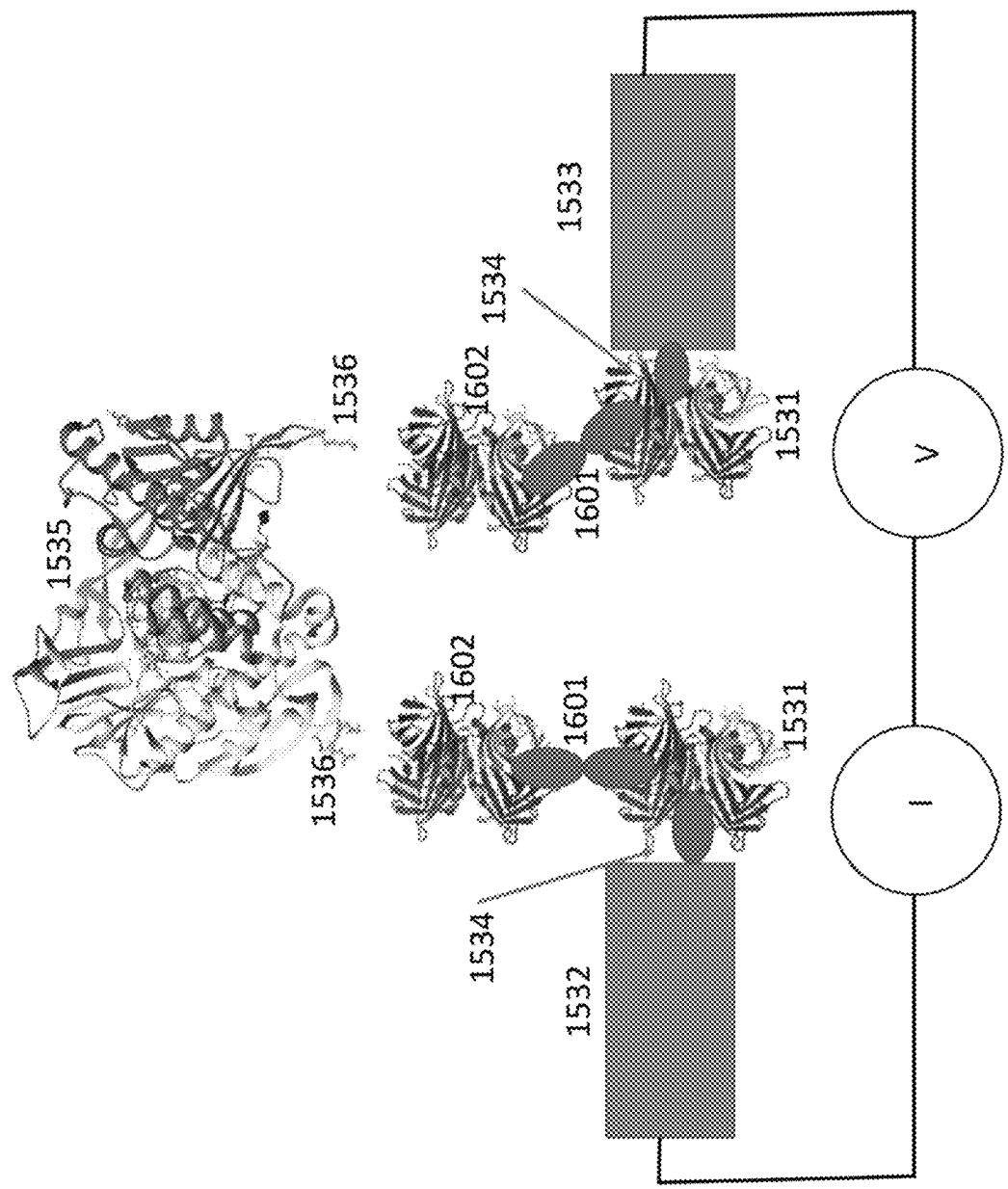
FIG. 16 shows a bioelectronic circuit in which the coupling is extended in distance by incorporating a second streptavidin and the bis-biotin molecule of FIG. 1.

The size of the gap over which protein conduction is monitored can be increased substantially at very little cost in conductivity by forming a daisy-chain of coupled proteins with each electrode as shown in FIG. 16. Here, a second coupling protein 1602 is added into the circuit, coupled to the first 1531 by means of a bivalent linker 1601 such as the bis-biotin shown in FIG. 1.

EXAMPLES

The following examples are presented for illustrative purposes and should not serve to limit the scope of the disclosed subject matter.

Sources of Materials

RGD peptide (cyclo(Arg-Gly-Asp-D-Phe-Cys)) was purchased from Peptides International (Louisville, Kentucky). Peptide ligands for the anti-HIV antibody and the anti-Ebola antibody were synthesized by CPC Scientific (Sunnyvale, California) with a purity >95%. DNP and biotin disulfides were synthesized in our lab (SI Appendix Figs. S10 and S13) and reduced for 2 h before use by an immobilized TCEP (Tris[2-carboxyethyl] phosphine hydrochloride) disulfide reducing gel from Thermo Scientific (cat #77712) following the manufacturer's instructions. Preparation of the solutions used in this disclosure is described in the SI Appendix. Anti-DNP antibody (mouse monoclonal IgE antibody), wild-type streptavidin and all other chemicals were purchased from Sigma Aldrich (Saint Louis, Missouri). Anti-HIV antibody (Anti-HIV1 p17 antibody [32/1.24.89]) and all the isotype controls were obtained from Abcam (Cambridge, MA). Anti-Ebola antibody was cultured from plants as described below. Binding affinities of all the three antibodies were measured by surface plasmon resonance (SPR). Thiolated streptavidin with an average of 2.5 thiols per tetramer was from ProteinMods (Madison, Wisconsin). Ag/AgCl reference electrodes salt-bridged by 3 M KCl or 10 mM KCl were prepared as described previously. B. Zhang et al., *Nano Futures* 1 (2017). Full details of the cyclic voltammetry are provided in the SI Appendix. The anti-Ebola antibody and the corresponding monomeric Fab fragment were prepared and purified as described in the Example 7.

Example 1. Synthesis of N,N'-bis-biotinyl-cystamine 11 (Chemical Structure Shown in FIG. 1)

Cystamine dihydrochloride (60 mg, 0.27 mmol) was added into DMF (2 mL), followed by the addition of triethyl amine (0.44 mL, 3.19 mmol). The mixture was stirred for 30 min, to which biotin NHS ester (0.27 g, 0.80 mmol) was added, and stirred at room temperature for 16 h. TLC indicted that cystamine was consumed and a product produced with an $R_f$ value of 0.63 in 20% methanol in DCM. The mixture was co-evaporated with dichloromethane until most of DMF and TEA was removed. The residue was separated on a column with a gradient of 0-20% methanol in DCM over 120 mins at a flow rate of 3 mL/min in an automated flash chromatography instrument Teledyne Isco. The product was obtained as a white solid (0.11 g and 67.1%). $^1$HNMR (400 MHz, DMSO-$d_6$): δ 1.20-1.60 (m, 12H), 2.07 (t, 7.6 Hz, 4H), 2.57 (d, 12.4 Hz, 2H), 2.77 (t, 6.3 Hz, 4H), 2.83 (dd, 5.1 and 12.6, 2H), 3.07-3.12 (m, 2H), 3.31 (t, 6.4 Hz, 4H), 4.11-4.15 (m, 2H), 4.31 (t, 5.2 Hz, 2H); $^{13}$CNMR (100 MHz, DMSO-$d_6$): δ 25.70, 28.50, 28.65, 35.62, 37.83, 38.37, 40.32, 55.92, 59.68, 61.52, 163.18, 172.69.

Example 2. Synthesis of Compound 20

Compound 20 was produced by exposing N,N'-bis-biotinyl-cystamine 11 for 2 h (immediately before use in devices) to an immobilized TCEP (Tris[2-carboxyethyl] phosphine hydrochloride) disulfide reducing gel from Thermo Scientific (cat #77712) following the manufacturer's instructions. The product (chemical structure shown in FIG. 2) was dissolved in 20% methanol in DCM, the solution that was subsequently used to modify electrodes.

Example 3. Functionalizing Substrates and STM Probes

Palladium substrates for STM measurement were prepared by evaporating a 200 nm palladium film onto a silicon wafer using an electron-beam evaporator (Lesker PVD 75), with a 10 nm titanium adhesion layer. The substrates were treated with a hydrogen flame immediately before functionalizing and then immersed in solutions of thiolated DNP, biotin, streptavidin or peptides containing a cysteine residue, overnight. Substrate functionalization with small ligands was characterized by Fourier transform infrared (FTIR) spectroscopy (Fig. S9) and ellipsometry. Coverage of the substrate was monitored by STM and AFM imaging.

STM probes were etched from a 0.25 mm Pd wire (California Fine Wires) by an AC electrochemical method. To avoid current leakage, probes were insulated with high-density polyethylene following the method described earlier for gold probes. M. Tuchband et al., *Rev Sci Instrum* 83, 015102 (2012). Each probe was tested by STM in 1 mM PB buffer at +0.5 V bias to ensure the leakage current was <1 pA. For functionalization, the probe was immersed in ligand solutions for 4 h or overnight. After that, it was taken out, rinsed with water, gently blown dry with nitrogen gas, and used immediately. Further details of the STM measurements are given in Example 4.

Example 4. STM Measurement

STM measurements were carried out on a PicoSPM scanning probe microscope (Agilent Technologies), coupled with a DAQ card (PCI-6821 or PCIE-7842R, National Instruments) for data acquisition. The Teflon cell, in which buffer solution and analytes were added, was cleaned with Piranha solution and then sonicated in Milli-Q water three times to remove residues (Note that Piranha solution is highly corrosive and must be handed with extreme care). In order to better control the surface potential, an Ag/AgCl reference electrode with 10 mM KCl salt bridge was connected onto the substrate. The probe was firstly engaged to 4 pA setpoint current with a bias of −0.2 V and then left to stabilize for 2 h before measurement. For STM IV sweep measurements, the servo system was first turned off and the probe was retracted by ΔZ nm with a speed of 1 nm/s. After that, the probe was suspended at that height for 1 minute, during which a custom Labview program was used to monitor the current change. Once the current exceeded a threshold of 50 pA, it was considered as a binding event and IV sweeps were started from −0.2 V to +0.2 V and then back, with a sweep rate of 1 V/s, followed by a 0.2 s resting. Subsequently, the current was checked again. If the current was still more than twice the noise level (6 pA), IV curves were continuously recorded until the bound protein molecule escaped. After one-minute of measurement, the servo system was turned on to re-engage the probe and then the whole process repeated. In each measurement, at least 1000 IV curves were collected, from which curves with overlapping up sweep and down sweep were selected (80% of the total) to construct the conductance distribution histogram. Current vs. time traces were recorded by another Labview program with a similar procedure except that the bias was held constant during the probe holding process. The analog-to-digital sampling rate is 50 KHz. Conductance measurement procedures for all the analytes were identical but with different efficiencies because of binding affinity and functionalization efficiency differences (Table S1).

TABLE S1

Frequency with which sweeps yielded an IV curve as a function of gap size and functionalization. $Z_0$~2.5 nm. No curves were obtained with control samples (Table 1).

| | Modifications | | | |
|---|---|---|---|---|
| Protein | Probe | Substrate | Gap size | Frequency |
| Anti-DNP | Thio-DNP | Thio-DNP | $Z_0$ + 1 nm | 70.1% |
| | Thio-DNP | Thio-DNP | $Z_0$ + 2 nm | 46.7% |
| | Thio-DNP | Thio-DNP | $Z_0$ + 3 nm | 22.8% |
| | Thio-DNP | Thio-DNP | $Z_0$ + 4 nm | 9.6% |
| | NA | Thio-DNP | $Z_0$ + 2 nm | ~0 |
| | MCE | Thio-DNP | $Z_0$ + 2 nm | 18.9% |
| Anti-HIV | Thio-peptide | Thio-peptide | $Z_0$ + 2 nm | 42.5% |
| | NA | Thio-peptide | $Z_0$ + 2 nm | ~0 |
| Anti-Ebola | Thio-peptide | Thio-peptide | $Z_0$ + 2 nm | 24.0% |
| | NA | Thio-peptide | $Z_0$ + 2 nm | ~0 |
| Integrin-$\alpha_v\beta_3$ | RGD peptide | RGD peptide | $Z_0$ + 1 nm | 35.9% |
| | RGD peptide | RGD peptide | $Z_0$ + 2 nm | 23.7% |
| | RGD peptide | RGD peptide | $Z_0$ + 3 nm | 10.5% |
| | NA | RGD peptide | $Z_0$ + 2 nm | ~0 |

TABLE S1-continued

Frequency with which sweeps yielded an IV curve as a function of gap size and functionalization. $Z_0 \sim 2.5$ nm. No curves were obtained with control samples (Table 1).

| Protein | Modifications | | | |
|---|---|---|---|---|
| | Probe | Substrate | Gap size | Frequency |
| Thio-Streptavidin | NA | Thio-Streptavidin | $Z_0$ | 48.2% |
| | NA | Thio-Streptavidin | $Z_0 + 1$ nm | 4.3% |
| Anti-Ebola Fab | Thio-peptide | Thio-peptide | $Z_0$ | 54.1% |
| | Thio-peptide | Thio-peptide | $Z_0 + 1$ nm | 11.8% |

Replicated measurements for each analyte were conducted with newly functionalized substrates and probes (Table S4). Potential relative to the reference electrode was set using a battery-powered voltage source connected between the substrate and reference electrode.

TABLE S4

Number of replications of each experiment

| Experiment | Times replicated |
|---|---|
| Anti-DNP antibody | 6 |
| Anti-Ebola antibody | 3 |
| Anti-HIV antibody | 3 |
| Integrin ($\alpha_v\beta_3$) | 4 |
| SH-Streptavidin | 5 |
| SH-Biotin + Free streptavidin | 2 |
| Anti-Ebola antibody Fab | 4 |

Example 5. Preparation of Solutions

Thiolated DNP and biotin were prepared in freshly degassed pure ethanol to a final concentration of 0.1 mM. Peptides were firstly dissolved in degassed water as received and then aliquoted and frozen at −80° C. Each time before use, one aliquot was taken out and diluted by degassed water to the desired concentration, usually 0.1 mM for substrate and probe functionalization. To lower the functionalizing density of DNP and peptides on the substrates, 2-mercaptoethanol (MCE) was added at 2 mM concentrations. Antibodies and isotype controls were aliquoted and stored at −80° C. and then diluted in 1 mM PB buffer (pH=7.4) before use. For STM and solid-state chip measurements, 100 nM antibodies or isotype controls in 1 mM phosphate buffer (PB) were used. Thiolated streptavidin of 1 μM in 1 mM PB buffer was prepared for substrate functionalization. Free biotin of 1 mM and wild-type streptavidin of 100 nM in 1 mM PB buffer were employed for the conductance measurements by STM. All the buffers and solutions were prepared in Milli-Q water with a conductivity of 18.2 MΩ. For all measurements, the 1 mM PB buffer (pH 7.4) was degassed with argon to avoid interference from oxygen.

Example 6. Cyclic Voltammetry

Pd substrates were cut into 0.5 cm×4.0 cm in size and used as the working electrode, with an active cell area of about 0.5 cm×1.0 cm. The substrate was treated with a hydrogen flame before functionalization. Cyclic voltammetry was performed on a potentiostat (Model AFCBP1, Pine Instruments), using a Pt wire as the counter electrode and an Ag/AgCl (3M KCl) as the reference electrode. The sweep range is from −0.5 V to +0.5 V, with a sweep rate of 10 mV/s unless stated otherwise.

Example 7. Expression and Purification of Anti-Ebola (EBOV) mAb 6D8 from *Nicotiana benthamiana* Plants The coding sequences of heavy and light chain of 6D8 (Lai, H., et al., *Plant Biotechnol J* 10, 95-104, doi:10.1111/j.1467-7652.2011.00649.x (2012) were cloned into MagnICON-based expression vectors. Lai, H. et al. *Proc Natl Acad Sci USA* 107, 2419-2424, doi:10.1073/pnas.0914503107 (2010). 6D8 was then transiently expressed in *N. benthamiana* plants as described previously. Yang, M., et al., *Plant Biotechnol J* 16, 572-580, doi:10.1111/pbi.12796 (2018). 6D8 mAb was isolated and purified to >95% homogeneity from *N. benthamiana* leaves by protein A affinity chromatography. Fulton, A. et al., *J Chromatogr A* 1389, 128-132, doi:10.1016/j.chroma.2015.02.013 (2015).

Example 8. Generation of Monomeric Fab of 6D8

Monomeric Fab fragments were prepared from 6D8 by using the Pierce Fab Preparation Kit (Thermo Scientific) according to the manufacturer's instructions (Thermos Scientific Pub. No. MAN0011651). Briefly, purified 6D8 was first incubated with papain immobilized to agarose beads at 37° C. for 6-12 hr. The digested mAb mixture was then recovered by centrifugation at 5000×g for 1 min and separated on a protein A chromatography column. The Fab fragment was recovered in the flow through fraction, while the Fc fragment and undigested mAb were trapped in the protein A column. The successful production of monomeric Fab was verified by SDS-PAGE analysis under both reducing and non-reducing conditions.

Single-Molecule Conductance Measurements

Reproducible two-point measurements of the conductance of molecules require reproducible contacts, (7) so the reproducible observation of large (nS scale) conductance fluctuations in single integrin molecules (bound to just one of two electrodes by their cognate ligands) was a surprising finding. (8) This prior work did not probe the low bias region (where fluctuations were absent) owing to leakage currents that obscured any DC current through the protein. Here, a scanning tunneling microscope (STM) was used to make single-molecule measurements in solution, systematically exploring the role of contacts, both specific and non-specific. With suitably insulated STM probes, (9) and potential control of the electrodes the background leakage current was reduced to less than 1 pA over the entire bias range. With adequate stabilization, the STM gap remained constant over periods of a minute so it was possible to disable the gap control servo, retract the tip, and record current-voltage (IV) curves. Up to 60 such curves (sweeping both up and down) were recorded before re-engaging the servo and repeating the process on another area of the substrate. In order to make two specific contacts, bivalent antibodies (an IgE and two IgG's) were used, each of which presents two binding sites, as well as streptavidin which binds up to four biotin molecules, so that epitope- or biotin-functionalized electrodes could be bridged by specific bonds. In the cases where bare metal electrodes were used, contacts were made to surface thiols on streptavidin modified with an average of 2.5 surface thiols per molecule. In addition, measurements were repeated using integrin, which can form a specific bond with only one of the two peptide-functionalized electrodes. Proteins and ligands are listed in Table 1.

Measured Conductances Depend on Contacts

Currents were only observed when the protein was bound specifically to at least one of the two electrodes Typically, no current was recorded for several seconds after retraction, after which the current jumped to a large (and variable) value in the presence of bound protein. Although the current fluctuates over minute time-scales, it is usually stable over a few seconds, so that 80% of the recorded curves on the sweep up are reproduced on the sweep down (data not shown). Controls (buffer alone or non-cognate proteins in solution) gave no signals. The rapidly fluctuating (ms-timescale) telegraph noise (TN) reported (8) for integrin was also observed for anti-DNP (data not shown), and all the other proteins studied above 0.1V. It is a ubiquitous signal of protein capture, showing the same two-level switching in all cases. These fluctuations were originally observed for a protein captured in a fixed junction chip (8) and though the present work uses an STM, measurements of TN were replicated for one of the proteins studied here (anti-DNP) in a chip as well as in the STM to show that these are not some artifact of the measurement method (data not shown). The voltage threshold for TN does not depend on gap until the contact is almost broken (data not shown) implying that it is associated with fluctuations of the contacts driven by a potential drop that occurs mostly at the contacts, as previously proposed (8) and discussed in more detail below.

With the exception of the TN, the response is linear, so that each IV trace can be characterized by a single conductance value, G. Measured distributions of G follow the log-normal distribution usually observed in single molecule measurements (data not shown). (10) The distributions are similar to distributions of current values obtained by recording current vs. time at a fixed gap and bias (data not shown) so the distribution was ascribed to different kinds of contact between the electrodes and the molecule. The distributions for integrin (gap=4.5 nm) and thio-streptavidin (gap=2.5 nm) have a single peak at about 0.3 nS (data not shown). Bare metal electrodes were used to capture the thiolated streptavidin, where the thiol mediated contacts displace the contamination on the electrode surfaces, (11) forming direct metal-molecule contacts. The integrin was captured by the cyclic RGD peptide at only one of the two electrodes, and no signals were observed unless both electrodes were functionalized. Functionalization with peptides allows for non-specific contacts with hydrophilic sites on the protein at the electrode that is not specifically coupled. The three antibodies yielded two conductance peaks (~0.3 nS and ~2 nS), suggesting two binding modes: NS-S as for the integrin, and the desired S-S when both antigen-binding sites bind specifically (data not shown). This interpretation was tested by replacing the peptides on one electrode with mercaptoethanol, making it hydrophilic and capable of forming an NS-S bridge. Only a single peak was observed (data not shown). As a further test, a Fab fragment from the anti-Ebola IgG was prepared with only a monovalent binding head. The fragment was too small to bridge the 4.5 nm gap, so the data were recorded in a 2.5 nm gap. There is only a single peak in the conductance distribution, reflecting the single NS-S contact (data not shown). Thus, the higher conductance peak must correspond to conduction via the two antigen binding sites. In order for this effect to be seen, the data set must be dominated by single molecule contacts. It is striking that the conductance of a single Fab fragment across a 2.5 nm gap is much smaller than the conductance of an antibody across a 4.5 nm gap (data not shown). This suggests that the intrinsic internal conductances of the proteins are much higher than the measured (contact-limited) values. This finding accounts for the previous reports of similar conductances measured for proteins of very different sizes. (12, 13)

Conductances do not Depend on Gap Size

The existence of an internal (through-molecule (14)) high-conductance path is illustrated by a series of measurements taken at different gap sizes, using the technique described above, but increasing the amount of the initial tip retraction (data not shown). Strikingly, the peak conductance values do not change with the gap size though the frequency with which data are accumulated falls (data not shown). This effect reflects the area of the probe available for contacts at a given height. Very few sites are available when the gap is comparable to the protein height (listed for similar structures found in the protein data base in Table 1). Gap-independent conductance has been reported before for azurin (see the SI of Ruiz et al. (15)) and a rod-like molecule trapped between a probe and a substrate. (14) As pointed out above, the contact point changes over the (~minute) course of a measurement, a reflection of the angstrom-scale change in the position of the STM probe. It is these various contact geometries that generate the overall shape of the conductance distributions (data not shown). Since the distributions retain the same peak positions and shapes at the different gap sizes, the data show no indications of proteins being "squeezed" at the smaller gap sizes.

Plots of the voltage thresholds for the turn on of TN as a function of gap size show that the voltage thresholds do not change significantly with the gap size. Thus, TN fluctuations must be driven by the local field at the metal-molecule interface, with relatively little potential dropped across the interior of the protein. This is also consistent with our finding that the lifetime of the TN is exponentially related to the peak current value, an observation that can be accounted for by a single "weak link" tunneling junction in the circuit that dominates the conductance. (8)

Conductance is Sensitive to Changes of Protein Structure

Figure 7A:
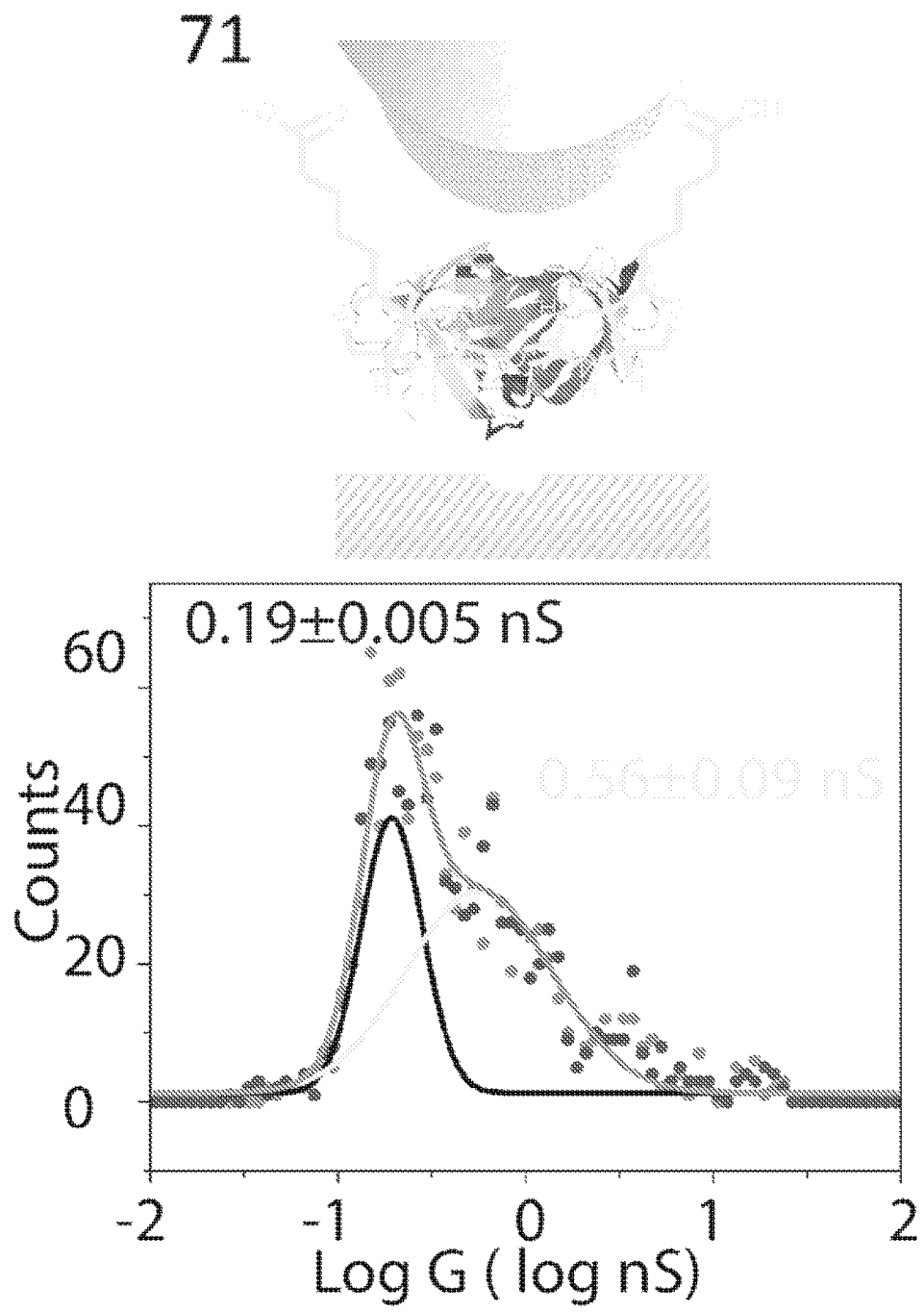

Since the conductance path follows the protein geometry, either internally, or along a surface contour, changes in protein geometry, and thus in the conduction path, could affect which contact points control the conductance. This would enable direct electrical sensing of structural changes of the protein This effect is demonstrated in FIG. 7A. Biotin complexation in a thiolated-streptavidin sample changes the conductance distribution significantly (FIG. 7A). A streptavidin molecule has four biotin binding sites, (16) so that the unthiolated apo-protein can be crosslinked by two biotins. A thiolated biotin was synthesized and functionalized both the probe and substrate with it (FIG. 7B), subsequently flowing apo-streptavidin into the sample cell. The consequent G distribution had three peaks, with the highest at nearly 7 nS. Thus, the measured conductance is sensitive to both local changes in protein structure and the chemical nature of the contact, showing how contacts are affected by structural changes of the protein. Thiolated streptavidin was attached to the substrate and probed with a biotinylated probe with similar results (data not shown) demonstrating that a single biotin-mediated contact is sufficient to generate the high conductance state at ~7 nS.

Possible Mechanisms

Electron tunneling decays far too rapidly to account for long-range transport. A tunneling conductance can be estimated from $G \sim G_0 \exp(-\beta x)$ where $G_0$ is 77 µS and $\beta \sim 1$ Å$^{-1}$. (24) For a small protein with x~4 nm, this yields $G<10^{-21}$ S, 12 orders of magnitude smaller than observed. To account for the observation of nS conductance over 10 nm distances would require a ($\beta$<0.1 Å$^{-1}$. In the well-studied case of DNA, thermally-activated hopping (17) leads to nearly-distance independent transport when the distance between the readily-ionized guanines exceeds three nucleotides. (18) Similar transport (via readily oxidized amino acids) has been observed in peptides. (19) In these cases, transport was limited by charge injection, and the ~1.5 eV barrier to charge injection was overcome using a chromophore excited with 630 nm (~2 eV) light. If a similar transport mechanism operates in the case of charge injection from electrodes, the barrier would be determined by the energy gap between the Fermi energy of Pd (work function 5.2 eV) and the absolute redox potential of the readily oxidized residues tyrosine and tryptophan. These potentials are ~+1 to +1.2 V vs. NHE (20) (21) so using 4.4 eV for the work function of the NHE (22) gives absolute potentials around 5.4-5.6 eV below the vacuum or a barrier of +0.2 to 0.4 eV with respect to the Fermi energy of Pd. Thus, a barrier of this magnitude must be overcome by the bond polarization associated with the binding of the protein to the electrode. This is well within the range of work-function changes observed for small molecules attached to a noble-metal surface by a thiol linkage. (23) Significant currents were obtained in three situations: (a) when contacts to both electrodes are via direct, thiol-mediated bonding; (b) when one bond is formed by specific binding to an epitope or ligand and another is formed by non-specific interactions between hydrophilic molecules attached to the electrode and the hydrophilic exterior of a protein and (c) the largest currents are observed when the protein is bound by recognition ligands at both electrodes (the ligand being linked via thiols to the electrodes in all cases). Weak, non-specific bonds do not result in significant current flow: at least one attachment must be via a covalent or ligand-mediated linkage. Thus, the barrier to charge injection is overcome by the binding of at least one specific ligand if the protein itself is not covalently modified to bind directly to the electrode.

Small changes in interfacial charge at a contact have been shown to affect transport strongly (24) and this is a variable we can change using potential control, albeit only over a small range if Faradaic currents are to be avoided. Presumably, small changes are dominated by a much larger field owing to bond polarization at the interface. In addition to the redox potentials of amino acid residues, the three-dimensional folding of the protein must play an important role. This is because small peptides that are stretched in a break junction do not conduct (25) whereas similar small peptides, folded on an electrode surface, do conduct. (26) This could be a consequence of some special geometry (27) or arrangement of hydrogen bonds. (28)

We turn finally to the fluctuations that set in above ±100 mV applied bias. The small dependence of this threshold voltage on gap size (data not shown) is consistent with the hypothesis that the internal conductance of the proteins is much higher than the conductance at the contacts, implying that these signals arise from voltage-driven fluctuations of the contacts themselves. We proposed such a mechanism in our earlier study of integrin (8) where we showed that the lifetime of the "on" states, $\tau$, was related to the peak current, $i_p$, of the telegraph noise peaks via $\tau \propto \ln(i_p)$, a relationship that can be explained by means of a single barrier determining both current and bonding strength. Once turned on, the current grows linearly with voltage, indicating that a new Ohmic conductance channel opens (data not shown). The turn-on process is described by an exponential of the form $$\exp\left(\frac{|V| - V_c}{kT/e}\right)$$

where $V_c$ is an activation voltage. Fits yield $V_c$~0.25V, a value characteristic of hydrogen bond strengths in water (29) suggesting that a hydrogen bond may be the 'weak link' in the circuit.

It is interesting to note that this 0.25V barrier is similar to the charge injection barrier deduced from the redox potentials of the amino acids, as discussed above. If the charge injection rate was limited by thermally activated hopping over a 0.22 to 0.47V barrier, and it is this rate that determines the conductance, then we would expect to observe a conductance of $$\approx G_0 \exp\left(-\frac{V}{ekT_B}\right)$$

where 0.22<V<0.47 volts, yielding from 12 nS to 0.5 pS, a range which encompasses the values reported here.

Role of Specific Binding in Electronic Conductance

We conclude that specific ligand-receptor interactions form good electrical connections to proteins. This is illustrated by the data shown in FIG. 7A and FIG. 7B. Connections made via covalent (thiol) modification of surface lysines directly bonded to the metal electrodes yield a lower maximum conductance (0.56 nS) than the non-covalent streptavidin-biotin coupling linked to the electrodes via a thiol-terminated ethane linkage (6.8 nS). This conductance is barely altered when only one biotinylated linker is used (data not shown). Thus, a weaker coupling to the hydrophobic interior of a protein is more effective that a stronger coupling to the hydrophilic exterior, even if only one such coupling is made. If, once injected, electrons move readily in the interior of the protein, then a second (non-specific) contact will act only as a barrier at the hydrophilic surface of the protein. Such a mechanism would account for the high conductance of integrin when bound by a ligand at only one site, and also for the complete lack of conductance when both contacts are non-covalent and non-specific.

REFERENCES

The following references are hereby incorporated by reference in their entireties:

U.S. patent application 62/673,080 (filed May 17, 2018).
U.S. patent application 62/682,991 (filed Jun. 10, 2018).
1. Wilner, I., E. Katz, A. Riklin, and R. Kasher, *Mediated electron transfer in glutathione reductase organized in self-assembled monolayers on Au electrodes.* J. Am. Chem. Soc., 1992. 114: p. 10965-10966.
2. Bostick, C. D., S. Mukhopadhyay, I. Pecht, M. Sheves, D. Cahen, and D. Lederman, *Protein bioelectronics: a review of what we do and do not know.* Reports on Progress in Physics, 2018. 81: p. 026601.
3. Adhikari, R. Y., N. S. Malvankar, M. T. Tuominen, and D. R. Lovley, *Conductivity of individual Geobacter pili.* RSC Advances, 2016. 6: p. 8354-8357.
4. Malvankar, N. S., M. Vargas, K. P. Nevin, A. E. Franks, C. Leang, B. C. Kim, K. Inoue, T. Mester, S. F. Covalla, J. P. Johnson, V. M. Rotello, M. T. Tuominen, and D. R. Lovley, *Tunable metallic-like conductivity in microbial nanowire networks.* Nat Nanotechnol, 2011. 6(9): p. 573-9.

5. Zhang, B., W. Song, P. Pang, H. Lai, Q. Chen, P. Zhang, and S. Lindsay, *The Role of Contacts in Long-Range Protein Conductance*. Proc Natl Acad Sci USA, 2019. submitted.
6. Vattay, G. a., D. Salahub, I. a. Csabai, A. Nassimi, and S. A. Kaufmann, *Quantum Criticality at the Origin of Life*. Journal of Physics: Conference Series 2015. 626: p. 012023.
7. Cui X D, et al. (2001) Reproducible measurement of single-molecule conductivity. *Science* (New York, N.Y.) 294(5542):571-574.
8. Nitzan A (2006) *Chemical dynamics in condensed phases* (Oxford University Press., Oxford).
9. Tuchband M, He J, Huang S, & Lindsay S (2012) Insulated gold scanning tunneling microscopy probes for recognition tunneling in an aqueous environment. *Rev Sci Instrum* 83(1):015102.
10. Chang S, et al. (2012) Chemical recognition and binding kinetics in a functionalized tunnel junction. *Nanotechnology* 23(23):235101
11. Smith T (1980) The hydrophilic nature of a clean gold surface. *J. Colloid Interface Science* 75:51-55.
12. Bostick C D, et al. (2018) Protein bioelectronics: a review of what we do and do not know. *Reports on Progress in Physics* 81:026601.
13. Nadav Amdursky, et al. (2014) Electronic Transport via Proteins. *Advanced Materials* 26:7142-7161.
14. Leary E, et al. (2011) Unambiguous one-molecule conductance measurements under ambient conditions. *Nano letters* 11(6):2236-2241.
15. Ruiz M P, et al. (2017) Bioengineering a Single-Protein Junction. *Journal of the American Chemical Society* 139 (43): 15337-15346.
16. Sano T & Cantor C R (1990) Cooperative biotin binding by streptavidin. *Journal of Biological Chemistry* 25:3369-3373.
17. Giese B & Spichty M (2000) Long distance charge transport through DNA: quantification and extension of the hopping model. *Chemphyschem* 1(4):195-198.
18. Giese B, Amaudrut J, Kohler A K, Spormann M, & Wessely S (2001) Direct observation of hole transfer through DNA by hopping between adenine bases and by tunnelling. *Nature* 412(6844):318-320.
19. Aubert C, Vos M H, Mathis P, Eker A P, & Brettel K (2000) Intraprotein radical transfer during photoactivation of DNA photolyase. *Nature* 405(6786):586-590.
20. Harriman A (1987) Further comments on the redox potentials of tryptophan and tyrosine. *Journal of Physical Chemistry* 91:6102-6104.
21. Odella E, et al. (2018) Controlling Proton-Coupled Electron Transfer in Bioinspired Artificial Photosynthetic Relays. *Journal of the American Chemical Society* 140 (45):15450-15460.
22. Tripkovic V, Björketun M E, Skúlason E, & Rossmeisl J (2011) Standard hydrogen electrode and potential of zero charge in density functional calculations. *Phys. Rev. B* 84:115452.
23. Alloway D M, et al. (2003) Interface Dipoles Arising from Self-Assembled Monolayers on Gold: UV-Photoemission Studies of Alkanethiols and Partially Fluorinated Alkanethiols. *J. Phys. Chem. B* 107:11690-11699.
24. Garg K, et al. (2018) Interface Electrostatics Dictates the Electron Transport via Bioelectronic Junctions. *ACS Appl Mater Interfaces*.
25. Xiao X, Xu B, & Tao N (2004) Conductance titration of single-peptide molecules. *Journal of the American Chemical Society* 126(17):5370-5371.
26. Guo C, et al. (2016) Tuning electronic transport via hepta-alanine peptides junction by tryptophan doping. *Proc Natl Acad Sci USA* 113(39):10785-10790.
27. Vattay Ga, Salahub D, Csabai Ia, Nassimi A, & Kaufmann S A (2015) Quantum Criticality at the Origin of Life. *Journal of Physics: Conference Series* 626:012023.
28. Lagunas A, et al. (2018) Long distance electron transfer through the aqueous solution between redox partner proteins. *Nat Commun.* 9:5157.
29. Jeffrey G A (1997) *An Introduction to Hydrogen Bonding* (Oxford University Press New York).

It will be apparent to those in the art that specific embodiments of the present disclosure may be directed to one or more of the above- and below-indicated embodiments in any combination.

While particular materials, formulations, operational sequences, process parameters, and end products have been set forth to describe and exemplify this invention, they are not intended to be limiting. Rather, it should be noted by those ordinarily skilled in the art that the written disclosures are exemplary only and that various other alternatives, adaptations, and modifications may be made within the scope of the present disclosure. Accordingly, the present disclosure is not limited to the specific embodiments illustrated herein but is limited only by the following claims.

What is claimed is:

1. A bioelectronic circuit comprising:
  (a) at least one electrode;
  (b) at least one ligand that is specific for a protein in a protein assembly, wherein the at least one ligand is modified so that it attaches to the at least one electrode, wherein the at least one ligand is selected from the group consisting of $HSCH_2CH_2$-dinitrophenol, CALDRWEKIRLR (SEQ ID NO: 1), CHNTPVYKLDISEATQV (SEQ ID NO: 2), cyclic RGDfC, thiolated-streptavidin, and $HSCH_2CH_2$-biotin; and
  (c) a protein assembly comprising a defined number of proteins that binds the at least one ligand, thereby forming an electronic contact between the at least one electrode and the protein assembly, wherein the protein assembly comprises at least one protein selected from the group consisting of a polymerase, an endonuclease, a helicase, and a proteosome.

2. The bioelectronic circuit according to claim 1, wherein the at least one electrode comprises a metal selected from the group consisting of palladium, platinum, and gold.

3. The bioelectronic circuit according to claim 1, wherein the protein assembly comprises at least one additional protein selected from the group consisting of IgE Anti-DNP, IgG Anti-HIV, IgG Anti-Ebola, Fab Anti-Ebola, $\alpha_V\beta_3$ Integrin, and streptavidin.

4. The bioelectronic circuit according to claim 1, wherein the at least one ligand is modified to comprise a thiol, amine, disulfide or cyanide moiety.

5. A bioelectronic circuit comprising:
  (a) a first electrode and a second electrode,
  (b) a first ligand and a second ligand that are specific for a protein in a protein assembly, wherein the protein in the protein assembly is modified to contain biotin, and wherein the first and second ligands are modified so that the first ligand attaches to the first electrode and the second ligand attaches to the second electrode, and
  (c) a protein assembly comprising a defined number of proteins that is modified to bind the first and the second ligands, wherein the binding of a protein in the protein assembly to the first and the second ligands forms an electronic contact between the electrode and the protein assembly.

6. The bioelectronic circuit of claim 5, wherein the first and/or the second ligand is a thiolated streptavidin.

7. The bioelectronic circuit of claim 5, wherein the protein is bis-biotinylated polymerase.

8. A bioelectronic circuit comprising:
  (a) a first electrode and a second electrode;
  (b) a first ligand that is specific for a protein in a protein assembly, wherein the first ligand is modified so that it attaches to the first electrode;
  (c) a protein assembly comprising a defined number of proteins that binds the first ligand and is modified to bind a second ligand; and
  (d) a second ligand that binds the protein assembly and is modified so that it attaches to the second electrode, thereby forming an electronic contact between the first and second electrodes and the protein assembly;
  wherein a binding site on the protein in the protein assembly that is bound to the first ligand is in proximity to a flexible linker sequence, and wherein a second binding site on the protein in the protein assembly that is bound to the second ligand is in proximity to a flexible linker sequence.

9. The bioelectronic circuit of claim 8, wherein the flexible linker sequence comprises GNSTNGTSNGSS (SEQ ID NO: 3).

10. A bioelectronic circuit comprising:
  (a) a first electrode and a second electrode;
  (b) a first protein, wherein the first protein is attached to the first electrode via biotin-streptavidin interactions;
  (c) a second protein, wherein the second protein is attached to the first protein via biotin-streptavidin interactions and is modified to bind a ligand; and
  (d) a ligand that binds the second protein and is modified so that it attaches to the second electrode, thereby forming an electronic contact between the first and second electrodes and the first and second protein.

11. The bioelectronic circuit according to claim 10, wherein the first protein comprises two biotins.

12. The bioelectronic circuit of claim 11, wherein the second protein comprises two biotinylated peptide sequences comprising SEQ ID NO: 4.

13. A method for detecting activity of at least one protein in the protein assembly of claim 5, claim 8, or claim 10, the method comprising introducing a substrate of the at least one protein in the protein assembly to the bioelectronic circuit of claim 5, claim 8, or claim 10, wherein generation of polymerized product indicates that the at least one protein in the protein assembly is active.

14. A method for detecting activity of at least one protein in the protein assembly of claim 5, claim 8, or claim 10, the method comprising introducing a substrate of the at least one protein in the protein assembly to the bioelectronic circuit of claim 5, claim 8, or claim 10, and detecting electrical changes.

15. A system for electrical measurement of protein activity comprising:
  (a) a bioelectronic circuit of claim 5, claim 8, or claim 10;
  (b) a means for applying a bias between the first electrode and the second electrode; and
  (c) a means for detecting current through the bioelectronic circuit of claim 5, claim 8, or claim 10.

* * * * *